United States Patent
Nishiuchi et al.

(10) Patent No.: US 9,308,394 B2
(45) Date of Patent: Apr. 12, 2016

(54) PARTICLE BEAM IRRADIATION SYSTEM AND OPERATING METHOD

(71) Applicant: HITACHI, LTD., Tokyo (JP)

(72) Inventors: Hideaki Nishiuchi, Hitachinaka (JP); Masumi Umezawa, Mito (JP); Takuya Nomura, Hitachi (JP); Satoshi Totake, Tokai (JP); Koji Tobinaga, Tokai (JP); Tomohisa Imagawa, Tokai (JP); Seiji Yoshiura, Hitachinaka (JP); Moemi Takeda, Tokai (JP)

(73) Assignee: HITACHI, LTD., Tokyo (JP)

(*) Notice: Subject to any disclaimer, the term of this patent is extended or adjusted under 35 U.S.C. 154(b) by 61 days.

(21) Appl. No.: 13/945,041

(22) Filed: Jul. 18, 2013

(65) Prior Publication Data
US 2014/0021375 A1    Jan. 23, 2014

(30) Foreign Application Priority Data

Jul. 19, 2012  (JP) ................................ 2012-160706
Jul. 31, 2012  (JP) ................................ 2012-170400

(51) Int. Cl.
*A61N 5/10*    (2006.01)
(52) U.S. Cl.
CPC ............ *A61N 5/1048* (2013.01); *A61N 5/1077* (2013.01); *A61N 2005/1087* (2013.01)
(58) Field of Classification Search
CPC ................ H05H 13/04; A61N 5/1048; A61N 2005/1074; A61N 5/1077
USPC ............................. 250/492.1, 492.3; 315/503
See application file for complete search history.

(56) References Cited

U.S. PATENT DOCUMENTS

| | | | |
|---|---|---|---|
| 8,742,699 B2 | 6/2014 | Umezawa et al. | |
| 2005/0139787 A1 | 6/2005 | Chiba et al. | |
| 2009/0296885 A1* | 12/2009 | Boeh et al. | 378/65 |
| 2014/0152199 A1* | 6/2014 | Arita | H05H 7/04 315/503 |

(Continued)

FOREIGN PATENT DOCUMENTS

| | | |
|---|---|---|
| EP | 2 384 099 A2 | 11/2011 |
| JP | 2008-226740 A | 9/2008 |

(Continued)

OTHER PUBLICATIONS

Chu et al., "Instrumentation for treatment of cancer using proton and light-ion beams", Review of Scientific Instruments, Aug. 1993, pp. 2074-2093, vol. 64, No. 8.

(Continued)

*Primary Examiner* — Jack Berman
*Assistant Examiner* — Kevin Chung
(74) *Attorney, Agent, or Firm* — Mattingly & Malur, PC

(57) ABSTRACT

A particle beam irradiation system having a multi-energy extraction control operation that controls the extraction beam energy in a synchrotron within a short time, such that when the ion beam irradiation is halted, an operating cycle is updated within a short time and a dose rate is improved. To this end, operating control data for each of the devices constituting the synchrotron is constructed by multi-energy extraction control pattern data for controlling extraction of beams of a plurality of energy levels at one operating cycle, and a plurality of sets of deceleration control data that correspond to the extraction control of the beam of the plurality of energy levels. The devices are controlled by using the operating control data.

25 Claims, 13 Drawing Sheets

(56) References Cited

U.S. PATENT DOCUMENTS

2015/0031931 A1* 1/2015 Nishiuchi ............ A61N 5/1067
 600/1
2015/0060703 A1* 3/2015 Ogasawara .......... A61N 5/1048
 250/492.3

FOREIGN PATENT DOCUMENTS

| JP | 2009-117111 A | 5/2009 |
| JP | 2010-238463 A | 10/2010 |
| JP | 2011-124149 A | 6/2011 |
| JP | 2011-233478 A | 11/2011 |
| JP | 4873563 B2 | 12/2011 |

OTHER PUBLICATIONS

Iwata et al., "Multiple-energy operation with extended flattops at HIMAC", Nuclear Instruments and Methods in Physics Research A 624, 2010, pp. 33-38.

Japanese Office Action received in corresponding Japanese Application No. 2012-160706 dated Dec. 1, 2015.

Japanese Office Action received in corresponding Japanese Application No. 2012-170400 dated Feb. 2, 2016.

* cited by examiner

PRIOR ART

PARTICLE BEAM IRRADIATION SYSTEM AND OPERATING METHOD

BACKGROUND OF THE INVENTION

The present invention relates to particle beam irradiation systems suitable for particle beam therapy using such a charged particle beam (ion beam) as of protons or heavy ions. More particularly, the invention is directed to a particle beam irradiation system configured to achieve beam energy change control and operating cycle update within a short time, and to a method for operating the system.

Particle beam therapy, a treatment performed upon the cancer in a patient by irradiating the affected region with such an ion beam as of protons or heavy ions, is known as radiation therapy for cancer. Useable methods for ion beam irradiation include such a scanning irradiation method that is disclosed in REVIEW OF SCIENTIFIC INSTRUMENTS, VOLUME 64, NUMBER 8 (AUGUST 1993), pp. 2074-2093 (hereinafter referred to as Non-Patent Document 1).

In addition, examples of a control method that realizes the beam energy change control required in a scanning irradiation method within a short time when a synchrotron is employed as an ion beam generator, include such multi-energy extraction control operation that is disclosed in JP-4873563-B and JP-2011-124149-A as well as Nuclear Instruments and Methods in Physics Research, A624 (2010), pp. 33-38 (hereinafter referred to as Non-Patent Document 2). In the multi-energy extraction operation, irradiation of ion beams of a plurality of energy levels is achieved within one operating cycle of the ion synchrotron.

SUMMARY OF THE INVENTION

In the scanning irradiation method, irradiation control for the irradiation field (hereinafter, referred to as the layer) in a depth direction of the affected region is implemented by controlling an energy level of the ion beam to be used for irradiation. To enhance the dose rate used when the scanning irradiation method is applied, therefore, changing the ion beam energy supplied from the ion beam generator needs to be accomplished within a short time. In the scanning irradiation method, since it is also necessary to control the irradiation beam energy according to a particular size (depth from the patient's body surface) of the affected region, a combination of irradiation beam energy levels needs to be controlled for each patient who is to be subjected to irradiation or for each affected region that is to be irradiated.

When a synchrotron is adopted as the ion beam generator, successive operations of injection, acceleration, extraction, and deceleration are controlled as one operating cycle. The repetition of ion beam energy change control, as in the scanning irradiation method, poses a problem that since the synchrotron requires the updating of its operating cycle, an energy change tends to be a time-consuming task. As described in JP-4873563-B and Non-Patent Document 2, examples of the multi-energy extraction control operation which involves extracting the beams of a plurality of energy levels within one operating cycle are introduced as measures for improving such a problem. According to Non-Patent Document 2, for example, the affected region can be irradiated with all beam energy levels useable in one operating control sequence, by providing one integrated set of operating control data that covers all energy levels available for the irradiation with the synchrotron, and extracting the beams with a flat top being extended only at the energy level to be irradiated. Additionally, since the beams of all useable energy levels can be irradiated in one operating control sequence, the synchrotron always allows the irradiation with the same operating control data, which offers an effect in that the operating control of the synchrotron in a particle beam therapy system is simplified.

To effectively realize the operating control proposed in JP-4873563-B and Non-Patent Document 2, a sufficient amount of electric charge for irradiating the affected region with beams of all energy levels in one operating control sequence is required to be stored within the synchrotron. For example, if for whatever reason the amount of stored beam charge required for therapeutic irradiation is not obtained during acceleration control of the synchrotron, the amount of beam charge stored within the synchrotron will be exhausted midway in the preset irradiation energy range. In case of the beam charge stored within the synchrotron is exhausted, there is a need to update the operating control of the synchrotron by halting the ion beam irradiation and then shifting the operation from extraction control to deceleration control. If an integrated set of operating control data that covers all energy levels available for the irradiation with the synchrotron is applied as operating control data for the synchrotron, the operation cannot be directly shifted from extraction energy control to deceleration control since the continuity of the setting values needs to be secured. It becomes necessary, therefore, to update the control data relating to each energy level change conducted during the time required for the shift from extraction energy control to deceleration control. This shifting time from extraction energy control to deceleration control is one of the causative factors lowering the dose rate and obstructing the shortening of the treatment time required. Likewise, the operation cannot be directly shifted from extraction energy control to deceleration control if trouble with a constituent element or device of the particle beam irradiation apparatus results in the ion beam irradiation being halted.

If the integrated set of operating control data covering all energy levels available for the irradiation with the synchrotron is applied as the operating control data for the synchrotron, this leads to generating a wasteful time not contributing to beam irradiation. That is to say, the above generates the control time during shifting from the incident beam energy of the synchrotron to irradiation starting energy and the control time during shifting from irradiation ending energy to deceleration ending energy. Such a wasteful control time tends to occupy a high rate with respect to a beam irradiation time under the irradiation conditions that narrow an absorbed dose range (Spread-Out Bragg Peak, hereinafter expressed as SOBP) geared to the thickness of the affected region. This tendency keeps beam irradiation in a desired energy range from being conducted at a short operating cycle, and is another causative factor lowering the dose rate and obstructing the shortening of the treatment time. Since SOBP differs according to the patient subjected to irradiation and varies according to the affected region as well, it becomes necessary to select an irradiation energy level required for the formation of predetermined SOBP, and to control the updating of the appropriate operating control data for the selected irradiation energy level.

JP-2011-124149-A presents a controller for an accelerator equipped with hardware elements that supply information relating to a coil current needed to energize magnetic field coils of the accelerator. The hardware elements are a magnetic field reference generator, which outputs appropriate magnetic-flux density information according to an elapsed time, and a current reference converter, which calculates the coil current for generating a magnetic field appropriate for the magnetic-flux density information. JP-2011-124149-A also shows a control method in which the reference magnetic field generator achieves beam extraction of a plurality of energy levels within one operating cycle by generating an output of the magnetic-flux density information in a combination of four kinds of patterns (an initial boost pattern, a decremental pattern, an incremental pattern, and an ending pattern). According to JP-2011-124149-A, ion beams of a plurality of energy levels can be extracted within one operating cycle by combining the four kinds of magnetic-flux density patterns. This function allows the selection of the irradiation energy level required for the formation of predetermined SOBP. At the same time, however, timing in which the four kinds of patterns will be selected and output requires prior writing into a timing controller. Because of this, the above problem is not solved. That is to say, as in JP-4873563-B and Non-Patent Document 2, since a halt of ion beam irradiation does not allow direct shifting from extraction energy control to deceleration control, the control data relating to each energy change conducted during the shifting time from extraction control to deceleration control requires updating before the operation can be shifted to deceleration control (the ending pattern referred to as in JP-2011-124149-A).

A first object of the present invention is to provide a particle beam irradiation system and a method for operating the system in which in the multi-energy extraction control operation that realizes change control of an extraction beam energy in a synchrotron in a short time, when ion beam irradiation is halted, updating of an operating cycle is conducted in a short time and a dose rate is improved.

A second object of the present invention is to provide a particle beam irradiation system and a method for operating the system in which in the multi-energy extraction control operation that realizes control of an extraction beam energy change in a synchrotron in a short time, beam irradiation in a desired energy range is conducted at a short operating cycle and a dose rate is improved.

To achieve the first object, an aspect of the present invention is a particle beam irradiation system including a synchrotron constructed to accelerate and extract an ion beam, an irradiation apparatus adapted to irradiate the ion beam extracted from the synchrotron, and a controller including operation control data to control extraction of beams of multiple energy levels at one operating cycle and to enable rapid shifting to deceleration control from whatever energy level of the multiple energy levels, and configured to control devices constituting the synchrotron by using the operating control data. With such features, control of the extraction beam energy change in the synchrotron and updating of an operating cycle when ion beam irradiation is halted can be conducted in a short time and a dose rate is improved.

The system configuration is described in further detail below. The operating control data includes multi-energy extraction control pattern data corresponding to the beam extraction control of the plurality of energy levels and a plurality of sets of deceleration control data. The multi-energy extraction control pattern data includes a plurality of acceleration control sections for accelerating the beam to predetermined extraction energy levels and a plurality of extraction control sections for extracting the beam that has been accelerated to the predetermined extraction energy levels. The plurality of sets of deceleration control data correspond to the respective extraction energy levels of plurality of the extraction control sections. The controller conducts extraction control of the beam of the plurality of energy levels by having the plurality of sets of pattern data for multi-energy extraction control. In addition, the controller enables rapid shifting to deceleration control from whatever energy level by having the deceleration control data that correspond to the respective extraction energy levels of the plurality of extraction control sections.

Furthermore, the plurality of sets of deceleration control data provided along with the pattern data for multi-energy extraction control are constructed to take values corresponding to the respective extraction energy levels of the plurality of extraction control sections as initial data values, and values corresponding to incident energy level as final data values. The deceleration control data corresponding to a final extraction energy level, in the pattern data for multi-energy extraction control, may be included in the multi-energy extraction control pattern data as a deceleration control section of the pattern data of the multi-energy extraction control, or the data in all deceleration control sections may be collectively placed at a location having the plurality of sets of control data.

Moreover, since the plurality of extraction control sections of the pattern data for multi-energy extraction control comprise data that corresponds only to the energy levels required for treatment of each patient, a wasteful time that is not contributing to beam irradiation (i.e., the control time from the incident beam energy to the irradiation starting energy and the control time from the irradiation ending energy to the deceleration ending energy) is prevented to occur. Accordingly, the beam irradiation in a desired energy range is achieved at a short operating cycle and the dose rate is enhanced.

These sets of control data are stored in power supply controllers for the devices constituting the ion synchrotron, respectively. Control timing signals that manage control timing of the devices constituting the ion synchrotron are input to the power supply controllers, and switching control of the respective sections of the operating control data corresponding to beam acceleration and deceleration control in the synchrotron is executed in accordance with the control timing signals.

Each control timing signal is output from a timing system. Timing data that enables output synchronized with occurrence of the operating control data is stored within the timing system. The timing system receives an extraction permission command that is output from an interlock system to permit ion beam irradiation of a patient, an energy change command that is output in accordance with elapsed-time information on ion beam irradiation of the patient, a deceleration control command that is output in accordance with a state of each of the elements constituting the particle beam irradiation system, and an irradiation completion command indicating that the irradiation has been completed. The timing system has a function that outputs, in accordance with those commands, timing signals to switch the control data of the acceleration control section or deceleration control section of the operating control data. In addition, even in case of trouble with an element constituting the particle beam irradiation system, when the deceleration control command is output from the interlock system, the timing system and the relevant power supply controller, after completing updating of currently ongoing control data, select the deceleration control data corresponding to the energy level reached after completion of updating of currently ongoing control data, and execute control for shift to deceleration control. Thus, a particle beam irradiation system and a method for operating the system that achieves rapid and safe updating of the operating cycle can be provided.

In addition, in order to achieve the first object, in an another aspect of the present invention, the operating control data is constructed by a plurality of sets of module data including initial acceleration control data, a plurality of sets of extraction control data for extracting ion beams of a plurality of energy levels, a plurality of sets of energy change control data for interconnecting the plurality of sets of extraction control data, and a plurality of sets of deceleration control data corresponding to the respective extraction energy levels in the plurality of sets of extraction control data.

In this case, extraction control of the beams of the plurality of energy levels is conducted by combining the plurality of sets of module data, and rapid shift to deceleration control from whatever energy level is enabled by having the deceleration control data corresponding to the respective extraction energy levels in the plurality of sets of extraction control data. By executing multi-energy extraction control operation by combining the module data in this way, energy level change control of the beam extracted from the synchrotron can be conducted in a short time. Further, by enabling rapid shift to deceleration control from whatever energy level in the multi-energy extraction control operation, updating of an operating cycle when ion beam irradiation is halted can be conducted in a short time and a dose rate is improved and a treatment time can be reduced.

Moreover, since the plurality of set of extraction control data comprise data that corresponds only to the energy levels required for treatment of each patient, a wasteful time that is not contributing to beam irradiation (i.e., the control time from the incident beam energy to the irradiation starting energy and the control time from the irradiation ending energy to the deceleration ending energy) is prevented to occur. Accordingly, the beam irradiation in a desired energy range is achieved at a short operating cycle and the dose rate is enhanced.

More specifically, the plurality of sets of deceleration control data are each constructed to take values corresponding to the respective extraction energy levels in the plurality of sets of extraction control data as initial data values, and to take values corresponding to incident energy level of the synchrotron as final data values. This enables direct shifting from the extraction energy level to deceleration control when ion beam irradiation is halted.

The controller includes a timing system configured to output a plurality of control timing signals to manage control timing of the devices constituting the synchrotron, and a power supply controller configured to control each of the devices constituting the synchrotron, and the initial acceleration control data, plurality of sets of extraction control data, plurality of sets of energy change control data and plurality of sets of deceleration control data that constitute the operating control data are stored in the power supply controller. The power supply controller receives the plurality of control timing signals output from the timing system, and in accordance with the control timing signals, selects and updates the initial acceleration control data, the plurality of sets of extraction control data, the plurality of sets of energy change control data and the plurality of sets of deceleration control data.

The controller further includes an interlock system configured to output an extraction control command for permitting a start of extraction parameter setting control in the synchrotron, an energy change command that is output in accordance with elapsed-time information on ion beam irradiated to the patient, a deceleration control command that is output in accordance with a state of devices including the synchrotron and the irradiation apparatus and constituting the particle beam irradiation system, and an irradiation completion command indicating that the irradiation has been completed. In accordance with the extraction control command, energy change command, deceleration control command, and irradiation completion command that are output from the interlock system, the timing system selects an appropriate control timing signal from the plurality of control timing signals and outputs the selected timing signal.

The interlock system is configured to output the deceleration control command in a case that the amount of beam charge stored within the synchrotron is insufficient for the irradiation with the beam of next energy level after completion of extraction control of the beam of a certain energy level, as well as in a case that the next target energy level is absent after completion of extraction control of the beam of a certain energy level. Upon receiving the deceleration control command, the timing system selects a deceleration control startup timing signal from the plurality of control timing signals and outputs the deceleration control startup timing signal. Upon receiving the deceleration control startup timing signal, the power supply controller selects from the plurality of sets of deceleration control data the deceleration control data corresponding to the energy level upon completion of extraction control, and shifts to deceleration control.

Thus, even if the amount of beam charge stored within the synchrotron is insufficient and ion beam irradiation comes to a halt, directly shift to deceleration control is achieved and updating of the operating cycle can be conducted in a short time.

Furthermore, the interlock system is configured to output the deceleration control command in case of trouble with devices that constitute the particle beam irradiation system including the synchrotron and the irradiation apparatus, and upon receiving the deceleration control startup timing signal from the timing system, the power supply controller updates currently operative control data, then selects from the plurality of sets of deceleration control data the deceleration control data corresponding to the reached energy level after the control of the update, and shifts to deceleration control.

Thus, even if a constituent element of the particle beam irradiation system becomes abnormal and ion beam irradiation comes to a halt, directly shift to deceleration control is achieved and updating of the operating cycle can be conducted in a short time and safely.

In addition, the interlock system is configured to output the energy change command in the case that the next target energy level is present after completion of extraction control of the beam of a certain energy level, or that the reached energy level after completion of initial acceleration control or completion of energy change control disagrees with the next target energy level, and upon receiving the energy change command, the timing system selects the appropriate energy change control timing signal from the plurality of control timing signals and outputs the energy change control timing signal. Upon receiving the energy change control timing signal, the power supply controller selects from the plurality of sets of energy change control data the energy change control data corresponding to the certain energy level or reached energy level, and shifts to energy change control. Thus, when an energy change is to be conducted without extracting the beam, since there is no necessity for the updating control of the extraction control data (i.e., extraction parameter setting control and extraction parameter cancellation control), energy change control can be achieved in a short time and the dose rate can be enhanced.

The initial acceleration control data, the plurality of sets of extraction control data, the plurality of sets of energy change control data and the plurality of sets of deceleration control data that constitute the operating control data are constituted by time-series data relating to a current/voltage which is a control quantity assigned directly to the devices constituting the synchrotron. This makes parameter change computation unnecessary and simplifies the system configuration and control means.

Furthermore, in order to achieve the second object, the controller includes a storage device in which control data that includes the initial acceleration control data, the plurality of sets of extraction control data, the plurality of sets of energy change control data and the plurality of sets of deceleration control data that constitute the operating control data, and that enables extraction of beams of all energy levels corresponding to irradiation parameters for a plurality of patients assumed is stored as module data, and a power supply controller configured to control each of the devices constituting the synchrotron. when irradiation parameters for a specific patient are assigned for irradiation setup, the controller selects appropriate control data from the module data stored in the storage device, stores the selected control data into the power supply controller to construct the operating control data.

With such features, a wasteful time that is not contributing to beam irradiation (i.e., the control time from the incident beam energy to the irradiation starting energy and the control time from the irradiation ending energy to the deceleration ending energy) is prevented to occur. Accordingly, the beam irradiation in a desired energy range is achieved at a short operating cycle and the dose rate is enhanced and a treatment time can be reduced.

Effect of the Invention

According to the present invention, in the multi-energy extraction control operation that realizes change control of an extraction beam energy in a synchrotron in a short time, when ion beam irradiation is halted, updating of an operating cycle is conducted in a short time and a dose rate is improved so that the treatment time can be reduced.

In addition, according to the present invention, beam irradiation in a desired energy range is conducted at a short operating cycle and a dose rate is improved so that the treatment time can be reduced.

DESCRIPTION OF PREFERRED EMBODIMENTS

Hereunder, embodiments of the present invention will be described using the accompanying drawings.

First Embodiment

Figure 1:
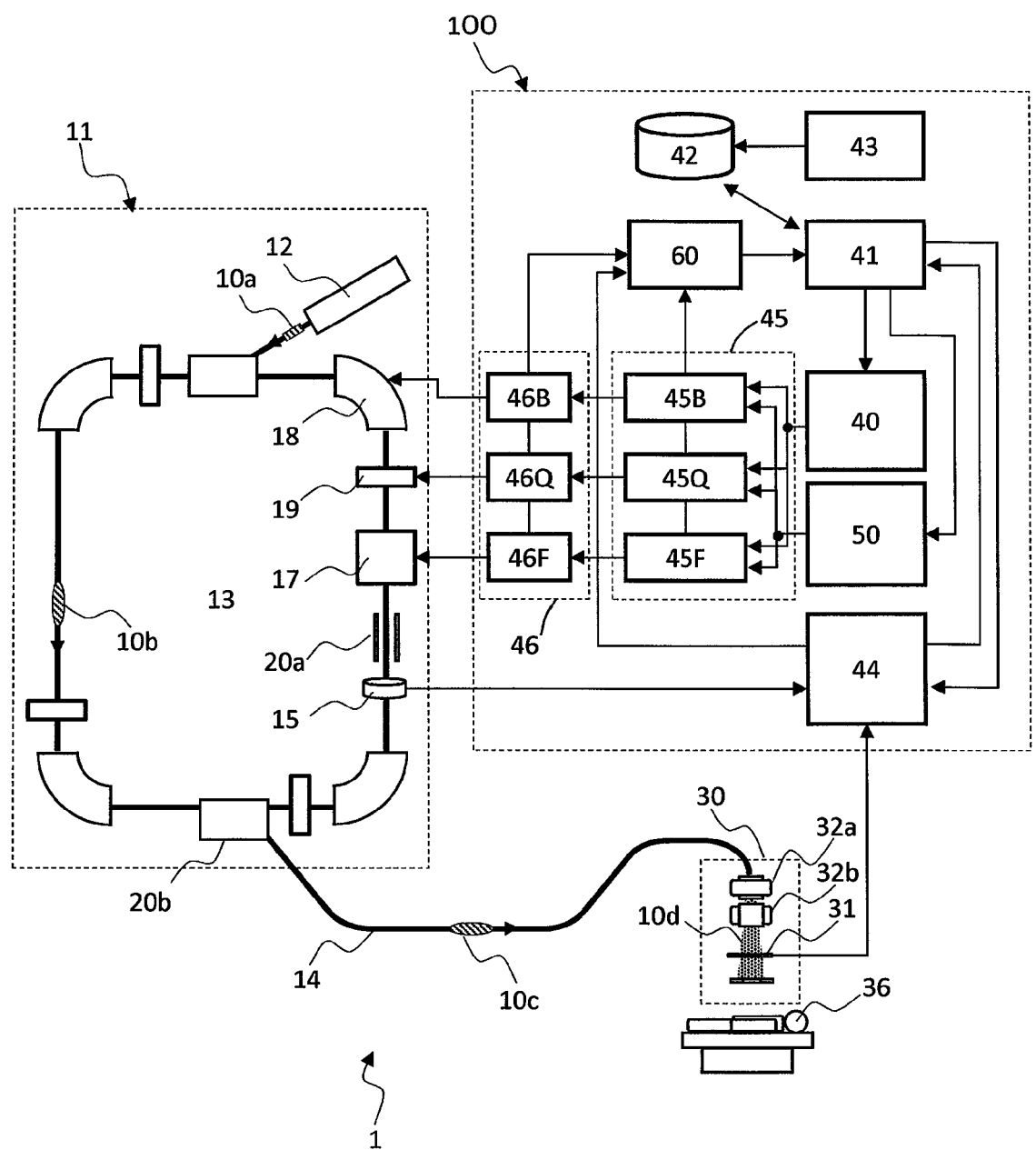
FIG. 1 is a diagram showing a configuration of a particle beam irradiation system which is a first embodiment of the present invention.

FIG. 1 is a diagram showing a configuration of a particle beam irradiation system according to a first embodiment of the present invention.

As shown in FIG. 1, the particle beam irradiation system 1 according to the present embodiment includes an ion beam generator 11, a beam transport apparatus 14, and an irradiation field forming apparatus (a charged-particle beam irradiation apparatus, hereinafter, referred to simply as the irradiation apparatus) 30. The beam transport apparatus 14 provides communication between the ion beam generator 11 and the irradiation apparatus 30 placed inside a treatment room.

The ion beam generator 11 includes an ion source (not shown), a pre-accelerator 12, and a synchrotron 13. The ion source is connected to the pre-accelerator 12, and the pre-accelerator 12 is connected to the synchrotron 13. The pre-accelerator 12 accelerates an ion beam 10, which has been generated by the ion source, to an energy level at which the ion beam can be injected into the synchrotron 13. The ion beam, after being accelerated by the pre-accelerator 12, is injected into the synchrotron 13 as an ion beam 10a.

The synchrotron 13 includes a radio-frequency accelerator (RF cavity) 17 that accelerates an orbiting ion beam 10b to a target energy level by applying a radio-frequency voltage to the ion beam 10b, extraction radio-frequency electrodes 20a that augment betatron oscillation amplitude of the orbiting ion beam, and an extraction deflector 20b that takes out the ion beam from the orbit.

Energy is applied to the beam 10b that has been injected into the synchrotron 13 by the radio-frequency voltage that has been applied to the RF cavity 17, and this beam is accelerated to the desired energy level. In order that the orbit of the ion beam 10b moving about inside the synchrotron 13 becomes constant during application of energy, magnetic field strength of bending magnets 18, quadrupole magnets 19, and other devices, and a frequency of the high-frequency voltage applied to the RF cavity 17 are enhanced according to the particular increase in the orbiting energy of the ion beam 10b.

The ion beam 10b accelerated to a desired energy level is applied to the extraction parameter setting control by which the amounts of excitation of the quadrupole magnets 19 and sextupole magnets (not shown) are controlled to establish parameters for permitting the orbiting beam 10b to be extracted (orbiting beam stabilization limiting parameters). After the extraction parameter setting control, an extraction radio-frequency voltage is applied to the extraction radio-frequency electrodes 20a to augment the betatron oscillation amplitude of the beam 10b orbiting inside the synchrotron 13. Because of the augmentation of the betatron oscillation amplitude, the orbiting beam 10b that has exceeded the stabilization limit parameters is extracted from the synchrotron 13 and directed to the beam transport apparatus 14, and then the beam is transported to the irradiation apparatus 30. Beam extraction control from the synchrotron 13 can be rapidly achieved by conducting ON/OFF control of the radio-frequency voltage applied to the extraction radio-frequency electrodes 20a.

After completing of beam extraction control from the synchrotron 13, the amounts of excitation of the quadrupole magnets 19 and sextupole magnets (not shown) are controlled by extraction parameter cancellation control, to cancel the stabilization limit parameters of the orbiting beam 10b formed during extraction parameter setting.

Upon completion of extraction parameter cancellation control, the magnetic field strength of the bending magnets 18, quadrupole magnets 19, and other devices, and the frequency of the high-frequency voltage applied to the RF cavity 17 are lowered to decelerate the ion beam 10b orbiting inside the synchrotron 13, and shift the synchrotron 13 to next operating cycle.

In accordance with a depth of an affected region from a body surface of a patient 36 and a shape of the affected region, the irradiation apparatus 30 controls an ion beam 10c that has been guided by the beam transport apparatus 14, and irradiates the affected region 37 of the patient 36 on a treatment couch. Scanning irradiation (shown in Non-Patent Document 1, page 2086, FIG. 45) is available as a method of irradiation, and the irradiation apparatus 30 employs the scanning irradiation method. Since the affected region 37 is directly irradiated with an ion beam 10d, the scanning irradiation method features high utilization efficiency of the ion beam 10d and hence, irradiation with the ion beam 10d that better matches the shape of the affected region than a conventional method of scatterer irradiation.

The adjustment of the beam range in a depth direction of the affected region is performed by changing the energy of the ion beam thereby to realize desired irradiation of the affected region. Particularly in the scanning irradiation method, the energy of the ion beam 10b orbiting inside the synchrotron 13 is controlled prior to extraction to adjust the beam range to the depth of the affected region 37, such that control of the energy change is required to be repeated a plurality of times during irradiation therapy of the patient. In addition, spot scanning irradiation, raster scanning irradiation, and the like are available as methods of beam irradiation in a planar direction of the affected region.

In the spot scanning irradiation method, a plane of the affected region to be irradiated is divided into dose management regions called spots, then after beam irradiation of each spot has been continued to obtain an irradiation dose set up with scanning stopped, the beam itself is also turned off, and the irradiation target position is moved to the next spot to be irradiated. In this manner, the starting position of irradiation is updated for each spot in the spot scanning irradiation method.

In the raster scanning irradiation method, although dose management regions are set up as in spot scanning irradiation, beam scanning is not stopped for each spot. Instead, the beam is scanned along the scan route during irradiation. For this reason, the irradiation dose per irradiating operation is reduced and repaint irradiation in which irradiation is repeated a plurality of times is executed for raised uniformity of the irradiation dose. In this manner, the starting position of the irradiation is updated for each scan route in the raster scanning irradiation method. In the spot scanning method, as in the raster scanning irradiation method, the irradiation dose to be delivered during one irradiating operation for one spot position may be set to be low and the plane to be irradiated may be scanned a plurality of times for a final irradiation dose to be reached.

Figure 2:
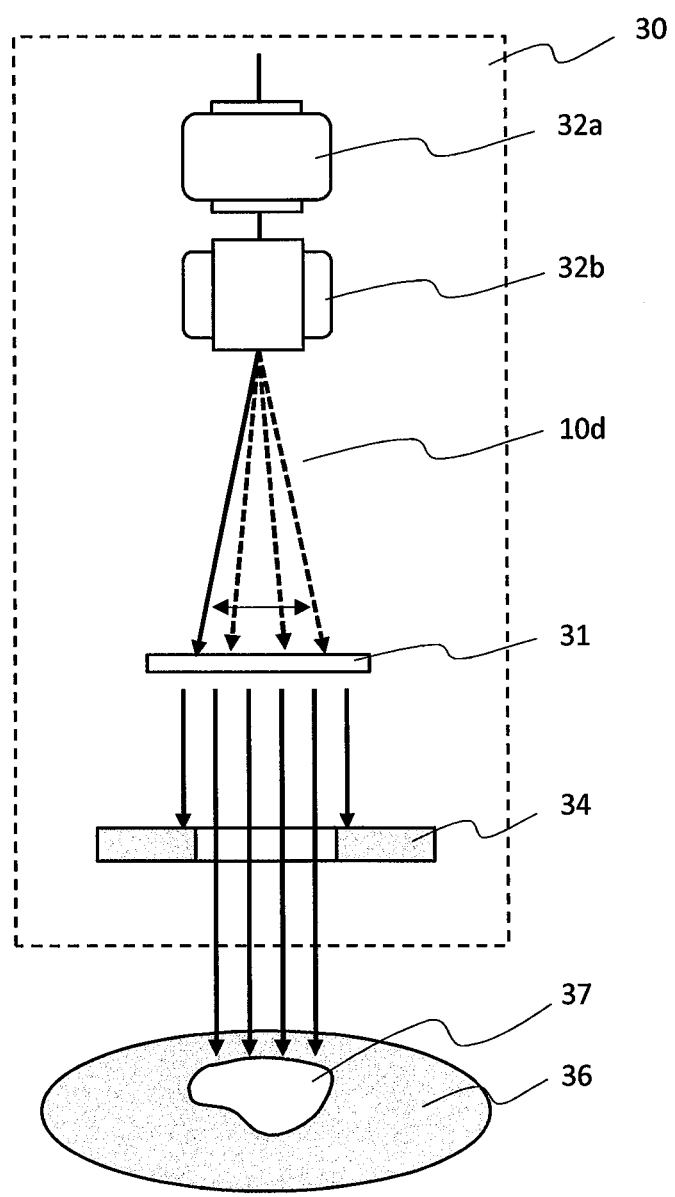
FIG. 2 is a diagram showing a configuration of a scanning irradiation apparatus employed in the first embodiment of the present invention.

FIG. 2 shows a configuration of the irradiation apparatus. The irradiation apparatus 30 includes scanning magnets 32a and 32b, and scans the beam along the plane of the affected region according to the shape of the affected region. The irradiation apparatus 30 also includes a dose monitor 31 that measures the irradiation dose of the beam 10d to be irradiated to the patient, and a beam shape monitor (not shown), and dose intensity and a shape of the beam 10d that has been irradiated are sequentially confirmed using the dose monitor 31 and the beam shape monitor. After being scanned by the scanning magnets 32, the beam 10d forms an irradiation field via a collimator 34, the irradiation field fitting the particular shape of the affected region 37 of the patient 36.

Referring back to FIG. 1, the particle beam irradiation system 1 according to the present embodiment includes a control system 100 (controllers). The control system 100 includes an accelerator controller 40 that controls the ion beam generator 11 and the beam transport apparatus 14, a total controller 41 that conducts total control of the entire particle beam irradiation system 1, a treatment planning device 43 that creates an irradiation condition for beam delivery to the patient, a storage device 42 for storage of the information that the treatment planning device 43 has planned, control information on the synchrotron 13, which is the ion beam generator, and the beam transport apparatus 14, and other information, an irradiation controller 44 that controls the constituent elements of the irradiation apparatus 30 and the irradiation dose of the ion beam 10d delivered to the affected region 37, a timing system 50 that implements synchronous control of the devices constituting the synchrotron 13, an interlock system 60 that is constructed independently of the total controller 41 so as to ensure safety for the patient 36, and a power supply controller 45 that controls a power supply 46 provided for each of the constituent devices of the synchrotron 13. The total controller 41 may include the storage device 42 as a part thereof.

The power supply 46 is a name referring collectively to power supplies for the plurality of devices constituting the synchrotron 13. A power supply 46B for each bending magnet 18, a power supply 46Q for each quadrupole magnet 19, and a power supply 46F for the RF cavity 17 are shown in FIG. 1 as the power supplies for the plurality of devices. The power supply controller 45 is likewise a name referring collectively to power supplies for the plurality of controllers corresponding to the plurality of devices. A controller 45B for the power supply 46B, a controller 45Q for the power supply 46Q, and a controller 45F for the power supply 46F are shown in FIG. 1.

Figure 8:
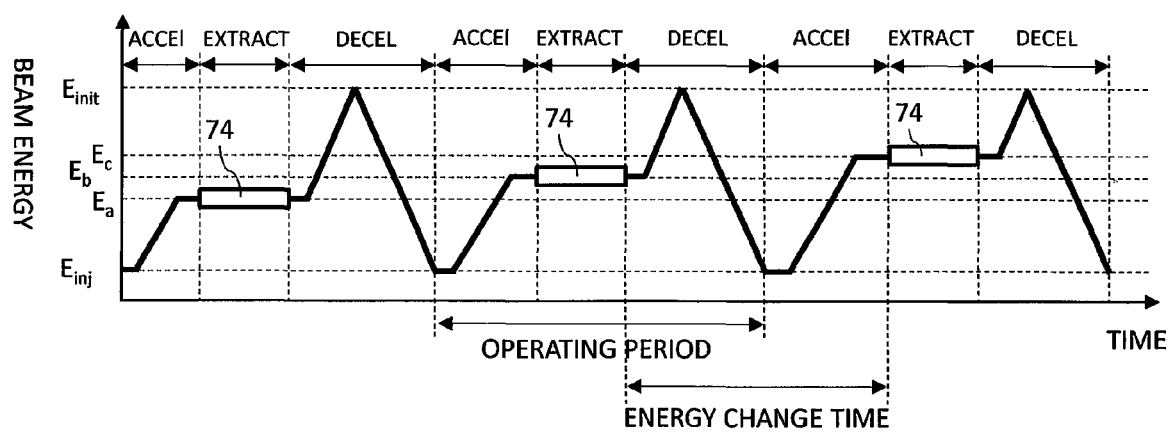
FIG. 8 is a diagram showing an operating sequence of a conventional synchrotron.

Items that the present inventors and others have reviewed/studied are described below using the description given in the foregoing documents relating to conventional techniques. FIG. 8 shows an operating sequence of a conventional synchrotron 13. The synchrotron 13 conducts successive controls of acceleration, extraction, and deceleration, within one operating cycle. Before and after extraction control, extraction parameter setting and extraction parameter cancellation are required. More specifically, extraction parameter setting control is required for the extraction of the ion beam inside the synchrotron, and extraction parameter cancellation control is required after extraction control.

In the operating control of the conventional synchrotron 13, the control data geared to the successive control cycles is provided as pattern data in a memory of a power supply controller 45 and the power supply controller 45 updates the control data in accordance with a timing signal 51 that is output from a timing system 50 which manages control timing of the devices constituting the synchrotron 13.

As shown in FIG. 8, the synchrotron 13 performs control from acceleration to deceleration within one operating cycle. To change the energy of the ion beam 10c extracted, therefore, the synchrotron needs to shift to deceleration control upon completion of extraction control, and then after decelerating a residual beam, update the operating cycle. The synchrotron achieves change control for a desired energy level by updating the operating cycle and then once again accelerating the ion beam 10b. The operating control of the conventional synchrotron 13, therefore, poses a problem in that since the energy change of the ion beam 10b requires substantially the same deal of time as one operating cycle, a treatment time tends to increase, which is liable to hinder the improvement of a dose rate.

Multi-energy extraction control operation of an ion synchrotron for realizing the extraction of ion beams of multiple energy levels within one operating cycle is introduced in JP-4873563-B. Such multi-energy extraction control operation enables an energy change time to be reduced in the scanning irradiation method.

Figure 3:
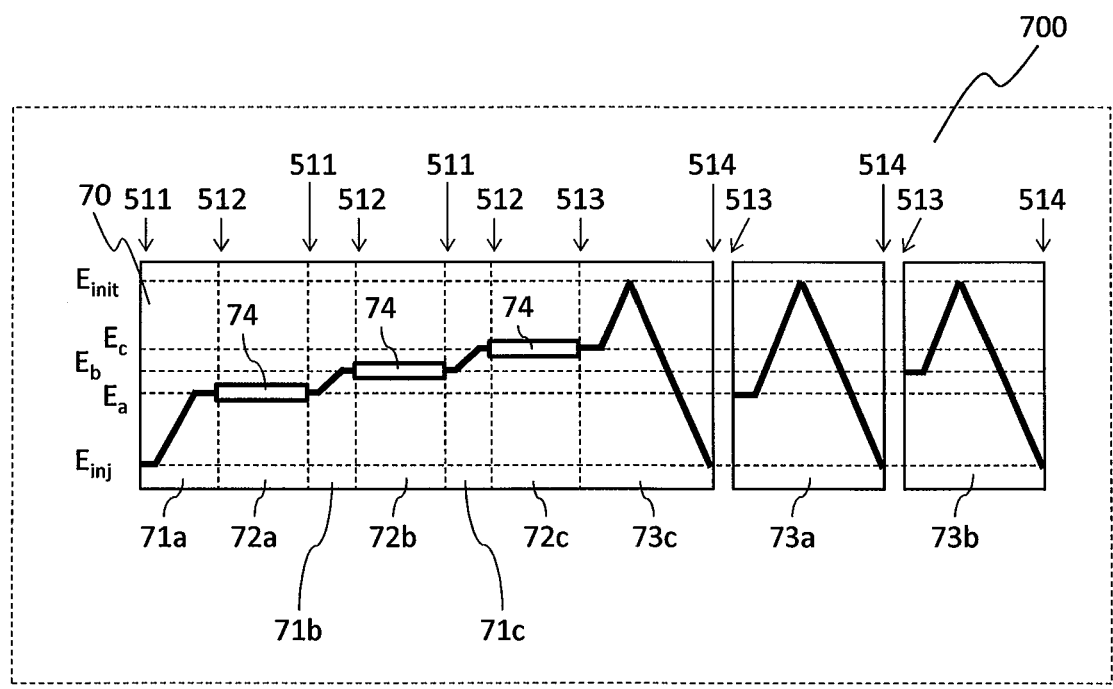
FIG. 3 is a diagram that shows composition of control data used in the first embodiment of the present invention.

Non-Patent Document 2 describes an operation method in which stepwise operating control data including energy change control and extraction control is provided in advance to suit a plurality of energy levels of beams to be extracted from an ion synchrotron (see Non-Patent Document 2, page 34, FIG. 2) and a flat section of the operating control data of the extraction control section corresponding to the energy level of the ion beam to be extracted is extended (see Non-Patent Document 2, page 35, FIG. 3).

As described in Non-Patent Document 2, when the control in which the operating control data enabling the plurality of energy levels of the beams to be extracted is provided in advance is applied, if the quantity of ion beams needed to complete all irradiating operations is stored within the synchrotron, this is effective since the irradiation with the beams of all the energy levels can be completed within one operating cycle. If the quantity of ion beams needed to complete all irradiating operations is not stored within the synchrotron, however, it is necessary, after the execution of deceleration control upon exhaustion of the ion beams, to update the operating cycle and then execute the injection and acceleration of the ion beam 10b once again. At this time, shifting the synchrotron from extraction control of the energy of the exhausted ion beams to deceleration control requires consideration of the continuity of the operating control data, and in turn requires updating of all the operating control data for energy change control stored in a location posterior to that of the data relating to the energy of the exhausted ion beam 10b. For these reasons, operation cannot be directly shifted from the operating control data to deceleration control. Accordingly, it becomes a time-consuming task to update the operating cycle of the synchrotron 13. If trouble occurs in a constituent element of the particle beam irradiation system 1, this likewise does not enable direct shifting from the operating control data to deceleration control.

JP-2011-124149-A presents a controller for an accelerator equipped with hardware elements that supply information relating to a coil current needed to energize magnetic field coils of the accelerator. The hardware elements are a magnetic field reference generator, which outputs appropriate magnetic-flux density information according to an elapsed time, and a reference current converter, which calculates the coil current for generating a magnetic field appropriate for the magnetic-flux density information. JP-2011-124149-A also shows a control method in which the magnetic field reference generator achieves beam extraction of a plurality of energy levels within one operating cycle by generating an output of the magnetic-flux density information in a combination of four kinds of patterns (an initial boost pattern, a decremental pattern, an incremental pattern, and an ending pattern). According to JP-2011-124149-A, ion beams of a plurality of energy levels can be extracted within one operating cycle by combining the four kinds of magnetic-flux density patterns. At the same time, however, a timing command signal for selecting operating control data for the synchrotron and specifying a combination sequence of the four kinds of patterns requires prior writing into a timing controller. This does not enable direct shifting from extraction energy control to deceleration control since the continuity of the data settings needs to be secured. In case of beam exhaustion and device trouble, therefore, rapid shifting to deceleration control might be inexecutable and updating the operating cycle of the synchrotron is likely to be a time-consuming task. Another problem is likely to occur. That is to say, since the reference current converter sequentially outputs the excitation currents of the bending magnets and quadrupole magnets while sequentially calculating these currents, a need arises to change arithmetic parameter settings with each pattern change and as a result, the device configuration and the control means are likely to become complex.

The present invention relates to the multi-energy extraction control operation of an ion synchrotron that enables it to extract ion beams of a plurality of energy levels within one operating cycle of the synchrotron. The invention provides the ion synchrotron in which the change control of the beam energy and the updating of the operating cycle can be achieved within a short time. The following describes details of the synchrotron.

First, a control data structure for the multi-energy extraction operation characterizing the present embodiment, and an operation sequence using the control data are described below using FIGS. 3 to 7A and 7B.

FIG. 3 is a diagram that shows composition of the operating control data relating to the devices constituting the synchrotron, the diagram also showing the excitation current of the bending magnets 18 as a typical example of the operating control data relating to the devices constituting the synchrotron. In actuality, as shown in Non-Patent Document 2, data of the number of levels corresponding to the number of energy levels of the beams delivered is provided, but the data described in the present embodiment is of three levels. In addition, while the operating control data that gives rise to sequential beam irradiation from lower energy levels to higher ones is shown in the present embodiment, substantially the same effects can also be obtained from sequential beam irradiation from higher energy levels to lower ones.

Figure 4:
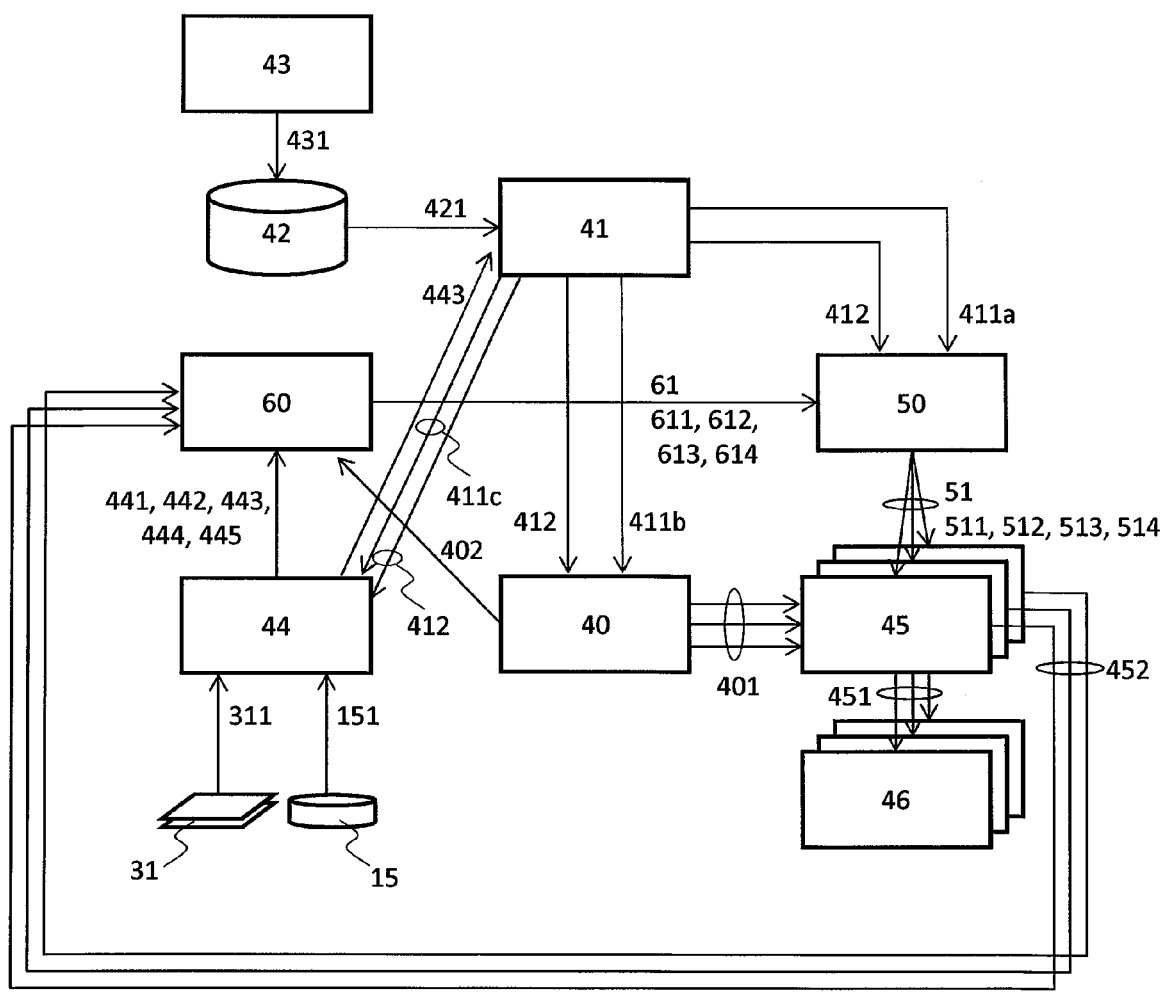
FIG. 4 is a diagram showing a flow of data transmission between controllers in the first embodiment of the present invention.
Figure 5:
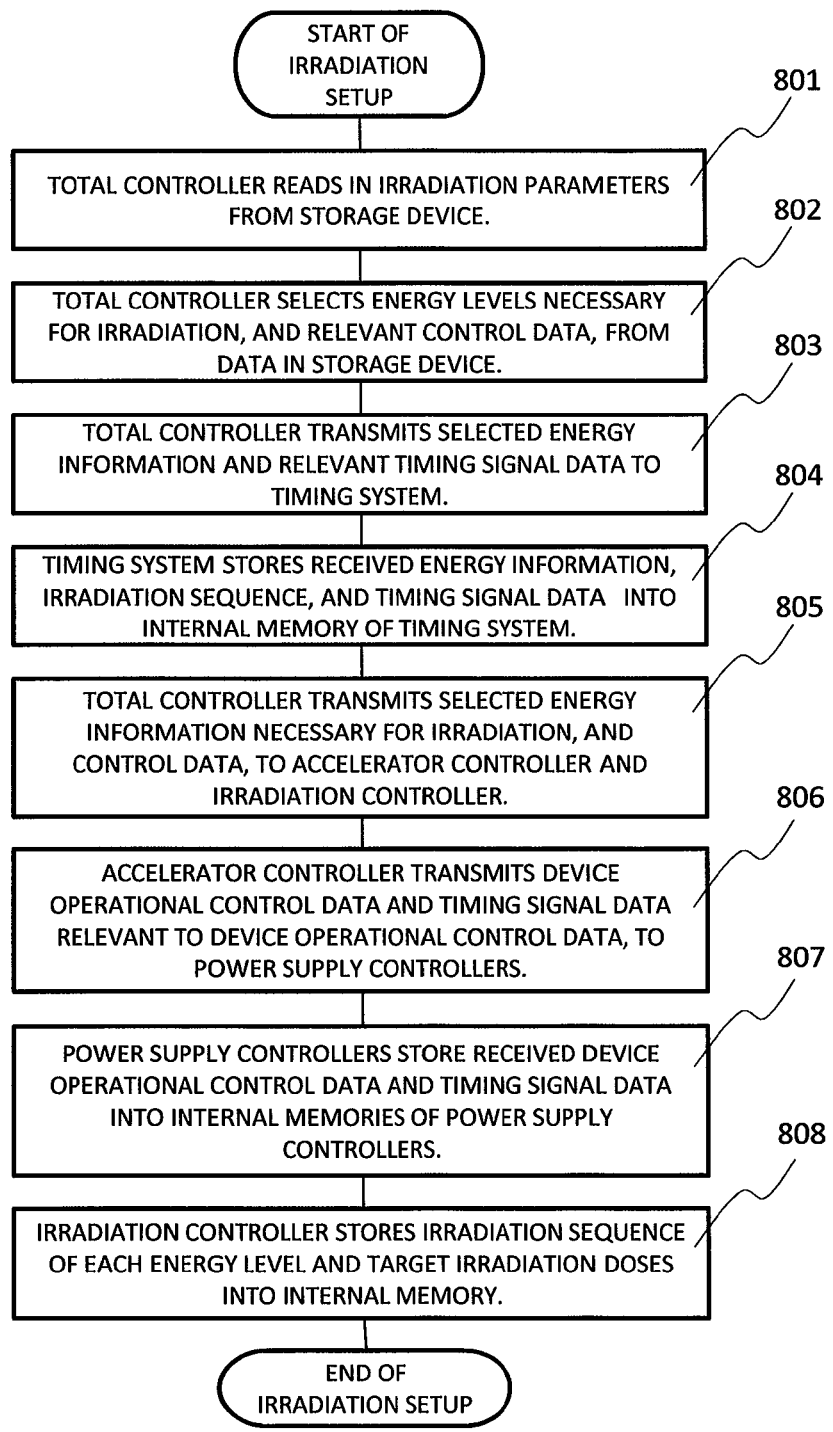
FIG. 5 is a diagram showing a flow of irradiation setup for multi-energy extraction control in the first embodiment of the present invention.
Figure 6:
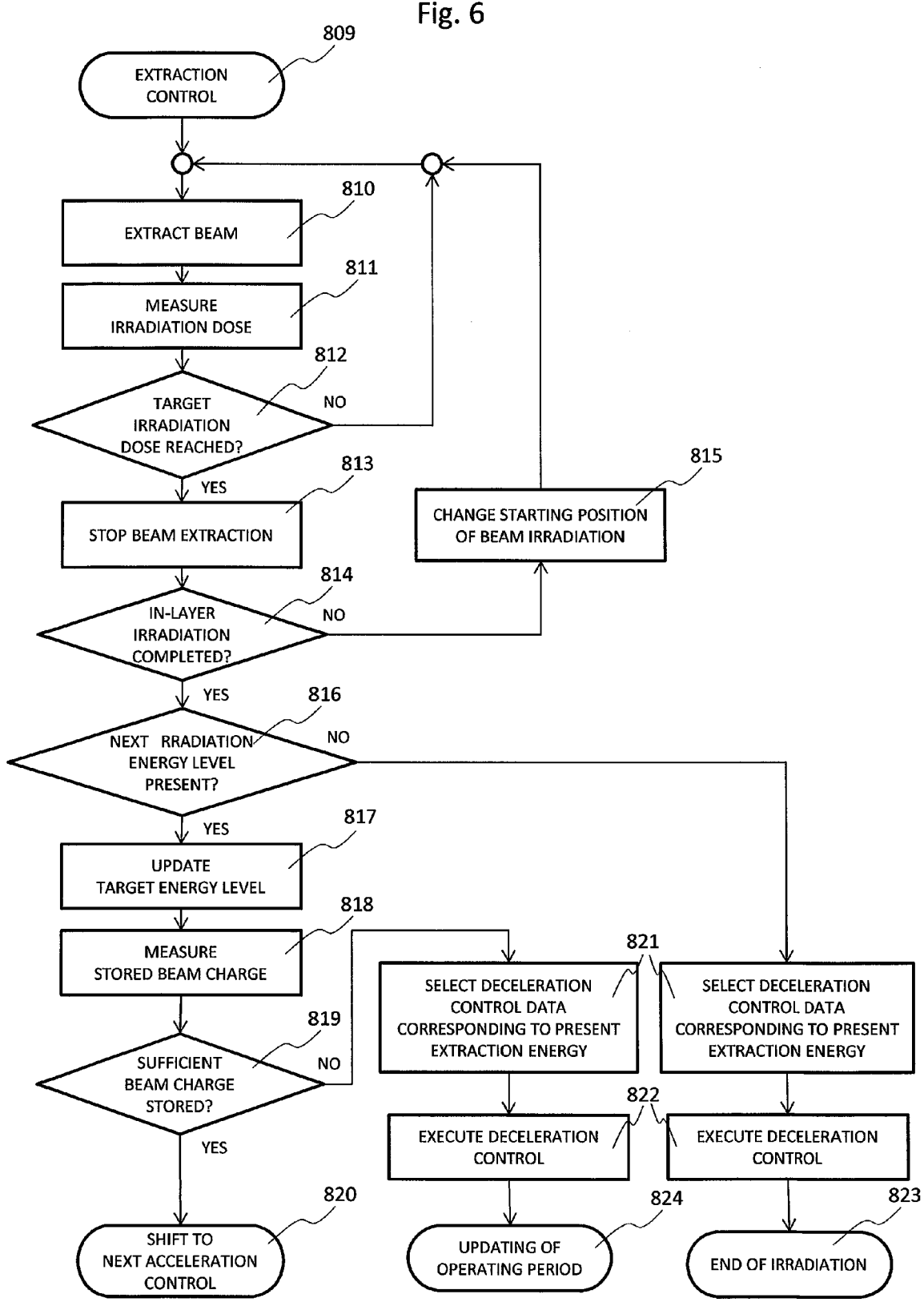
FIG. 6 is a diagram showing a flow of operating control for multi-energy extraction control in the first embodiment of the present invention.
Figure 7A:
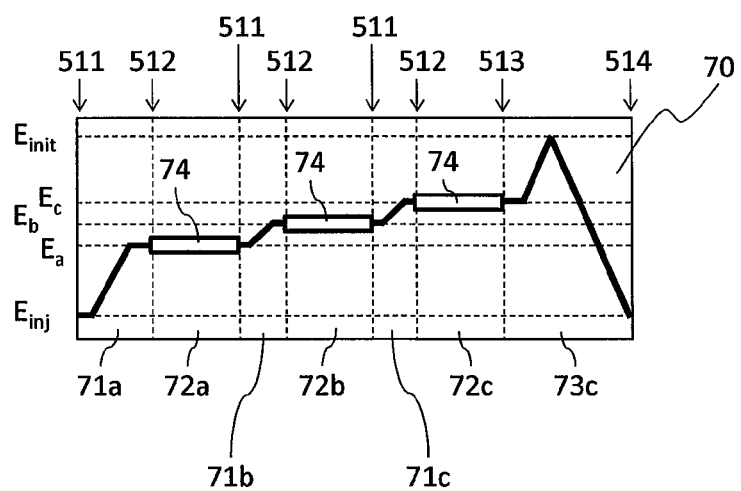
FIG. 7A is a diagram showing an example of control data output during multi-energy extraction control in the first embodiment of the present invention.
Figure 7B:
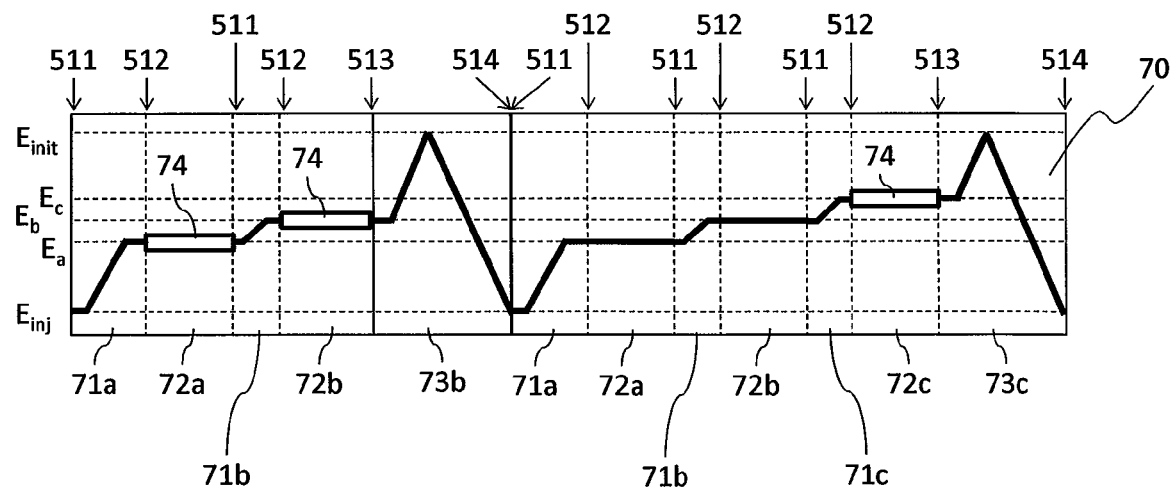
FIG. 7B is a diagram showing another example of control data output during multi-energy extraction operation in the first embodiment of the present invention.

FIG. 4 is a diagram showing a configuration of a control system 100 (controller) for achieving the multi-energy extraction operation characterizing the present embodiment. A flow of information transmission between the controllers or devices is also shown in FIG. 4. FIG. 5 is a diagram showing a flow of irradiation setup for the multi-energy extraction control. FIG. 6 is a diagram showing a flow of control for the multi-energy extraction control. FIGS. 7A and 7B show examples of control data output during the multi-energy extraction control using the operating control data shown in FIG. 3.

As shown in FIG. 3, operating control data 700 on the plurality of elements or devices constituting the synchrotron (in the shown example, operating control data on the bending magnets 18) includes multi-energy extraction control pattern data 70, which is used to control the extraction of the beams of a plurality of energy levels within one operating cycle, and a plurality of sets of deceleration control data, 73a and 73b, which correspond to extraction control of the beams of the energy levels. Extraction control of the beams of the plurality of energy levels is conducted by controlling the relevant devices (in the shown example, the bending magnets 18) by use of the multi-energy extraction control pattern data 70. In addition, the plurality of sets of deceleration control data, 73a and 73b, that correspond to extraction control of the beams of the energy levels are provided, which enables rapid shifting to deceleration control from whatever energy level.

The multi-energy extraction control pattern data 70 includes a plurality of sets of acceleration control data (acceleration control sections), 71a to 71c (hereinafter, represented as 71 where appropriate), a plurality of sets of extraction control data (extraction control sections), 72a to 72c (hereinafter, represented as 72 where appropriate), and deceleration control data (deceleration control section) 73c (hereinafter, represented as 73 where appropriate). Additionally, a plurality of sets of deceleration control data, 73a and 73b (hereinafter, represented as 73 where appropriate), are provided for the plurality of sets of extraction control data constituting a part of the multi-energy extraction control pattern data 70. The control data sets 71 to 73 are each provided as time-series data on a current/voltage which is a control quantity assigned directly to the relevant device. The control data relating to the bending magnets 18, for example, includes time-series data on the excitation current and voltage (not shown) that are set up for the bending magnet power supply 46B needed to generate predetermined bending magnetic field strength. The control data may include the time-series data relating to the bending magnetic field strength, and the time-series data relating to the bending magnetic field strength may be converted into the control quantity (current/voltage) assigned directly to the device during control. A plurality of sets of pattern data that are formed from different combinations of irradiation energy, for irradiation parameters relating to an assumed plurality of patients, are provided as the pattern data 70 for achieving multi-energy extraction operation, and these sets of pattern data 70, along with the relevant sets of deceleration control data 73, are prestored within the storage device 42. The pattern data 70 and deceleration control data sets 73a, 73b shown in FIG. 3 stored within the storage device 42 are the control data that has been selected according to the irradiation parameters for a specific patient and stored into the power supply controller 45.

The pattern data 70 may include the acceleration control section 71 and the extraction control section 72, and the deceleration control data 73 may be constructed so that each set of deceleration control data corresponding to all synchrotron-extractable beam energy levels that satisfy the irradiation parameters for the assumed plurality of patients is integrated as one set of deceleration control data 73. In this case, if all pattern data 70 corresponding to the irradiation parameters for the assumed plurality of patients is prestored into the storage device 42 and all deceleration control data 73 is prestored into the power supply controller 45, only the pattern data 70 relevant to the irradiation parameters for the patients may be sequentially selected from the storage device 42 and the selected pattern data may be stored into the power supply controller 45. This enables irradiation and thereby facilitates management of the operating control data for each irradiating operation on the patients. Additionally, if the deceleration control data 73 is prestored into the power supply controller 45, a capacity of the operating control data transmitted between the controllers can be reduced according to the irradiation parameters for each patient. The above also enables reduction in the time needed to update the operating control data when irradiation setup takes place.

The control data sets 71 to 73 in the operating control data 700 are associated with respective timing signals 51 that are output from the timing system 50 to the power supply controller 45. The timing signals 51 in the present embodiment include an acceleration control timing signal 511, an extraction control timing signal 512, a deceleration control startup timing signal 513, and a deceleration completion timing signal 514. Upon input of one such timing signal 51 to the power supply controller 45, the power supply controller 45 selects the control data set 71-73 associated with the timing signal 51, and starts data updating control from an initial address of the selected control data set 71-73.

Referring to FIG. 3, when the acceleration control timing signal 511 is input, the updating control of the acceleration control data set 71a from injection energy (Einj) to extraction energy (Ea) of an initial level is conducted and the beam is accelerated. When the extraction control timing signal 512 is input, the updating control of the extraction control data set 72a is conducted and an application process 74 for the extraction radio-frequency voltage is conducted upon the extraction radio-frequency electrodes 20a. Beam extraction is thus controlled. The irradiation controller 44 sequentially measures the irradiation dose 311 occurring during extraction control, then outputs a full dose signal 442 in accordance with the measured value and completes extraction control. Depending on the amount of stored beam charge at the completion of extraction control and on whether next irradiation energy is present, the irradiation controller 44 determines whether the timing system 50 outputs the acceleration control timing signal 511 to shift the pattern data to the next acceleration control data (i.e., shifting from 72a to 71b) or outputs the deceleration control startup timing signal 513 to shift the pattern data to the deceleration control data (i.e., shifting from 72a to 73a). To achieve this control, an ending value of the extraction control data 72 and a starting value of the acceleration control data 71 for accelerating the beam to the next irradiation energy (e.g., an ending value of 72a and a starting value of 71b in FIG. 3) are set to be the same value in the operating control data 700 so that both values can be continuously connected. The same also applies for the ending value of the extraction control data 72 and a starting value of the acceleration control data 73 for decelerating the beam to injection energy (e.g., the ending value of 72a in FIG. 3 and a starting value of 73a in the figure).

By achieving such control, the control data can be easily changed and updated according to the input of the timing signal 51.

In addition, when the multi-energy extraction operation described above is executed, the interlock system 60 outputs an interlock signal 61 based on an energy change request signal 443, a deceleration control request signal 444, and an irradiation completion signal 445, each output from the irradiation controller 44, and on status information, output from the power supply controller 45, to indicate whether the relevant devices are sound. The interlock signal 61 includes an energy change command 611, an irradiation completion command 612, and a deceleration control command 613. The timing system 50 outputs the acceleration control timing signal 511 in accordance with the energy change command 611 output from the interlock system 60. The timing system 50 also outputs the deceleration control startup timing signal 513 in accordance with the irradiation completion command 612 and the deceleration control command 613. In accordance with the acceleration control timing signal 511, the power supply controller 45 conducts the updating control of the acceleration control data 71 included in the pattern data 70, and in accordance with the deceleration control startup timing signal 513, the power supply controller 45 selects, of the deceleration control data sets 73a, 73b, 73c, only the deceleration control data corresponding to immediately previous extraction energy, and conducts the updating control of the selected acceleration control data.

A flow of irradiation setup for executing multi-energy extraction control using the control data shown in FIG. 3 that relates to the devices constituting the synchrotron is described below using FIGS. 4 and 5 together.

First, the treatment planning device 43 registers, in the storage device 42, treatment planning information 431 containing the irradiation parameters and others required for the treatment of the patient. In step 801, on the basis of the irradiation parameter setting information, the total controller 41 reads in the irradiation parameters 421 from the storage device 42. In step 802, using the irradiation parameters 421, the total controller 41 selects the energy information necessary for irradiation, target irradiation doses, an irradiation sequence and operation control data corresponding to the irradiation energy.

In step 803, the total controller 41 transmits control data 411a including the energy information necessary for irradiation, the irradiation sequence and timing signals corresponding to the energy information, to the timing system 50.

In step 804, the timing system 50 stores the control data 411a transmitted from the total controller 41 and including the energy information, irradiation sequence and timing signals corresponding to the energy information, into an internal memory of the timing system 50. In step 805, the total controller 41 likewise transmits control data set 411b, 411c including the energy information necessary for irradiation, the irradiation sequence, the operating control data for each constituent element or device and the timing signals corresponding to the operating control data, to the accelerator controller 40 and the irradiation controller 44. The control data set 411c transmitted to the irradiation controller 44 includes the irradiation sequence of each irradiation energy level and target irradiation doses.

In step 806, the accelerator controller 40 transmits control data 401 to each power supply controller 45 for each of the constituent devices of the synchrotron 13 and beam transport apparatus 14, the control data 401 including the operating control data for each device and the timing signals corresponding to the operating control data. In step 807, the power supply controller 45 stores the control data 401 into the memory. In step 808, the irradiation controller 44 stores the irradiation sequence of irradiation energy levels and the target irradiation doses into an internal memory.

Next, a flow of the beam extraction control conducted when multi-energy extraction control is executed using the control data shown in FIG. 3 that relates to the devices constituting the synchrotron is described below using FIGS. 4 and 6.

The power supply controller 45 uses the acceleration control data 71a to accelerate the beam from the injection energy level (Einj) to the extraction energy level (Ea), and the accelerator controller 40, after confirming the energy of the orbiting beam 10b, outputs an energy determination signal 402 to the interlock system 60. In step 809, the interlock system 60 outputs an extraction control command 614 to the timing system 50 to shift operating control to extraction control. In extraction control, the radio-frequency signal application process 74 is conducted upon the extraction radio-frequency electrodes 20a in accordance with an extraction control permission signal 441 from the irradiation controller 44. The beam is thus extracted (step 810). During extraction control of the beam, the irradiation controller 44 uses the dose monitor 31 to measure the dose 311 delivered to the affected region (step 811), and sequentially determines whether the irradiation dose 311 has reached its target value, that is, whether irradiation target dosing has been completed (step 812). The target dose here refers to a dose to be applied to one spot position in one irradiating operation in the case of spot scanning, or a dose to be applied when a scan route is irradiated once in the case of raster scanning. Upon the irradiation dose 311 being reached, the radio-frequency voltage application process 74 for the extraction radio-frequency electrodes 20a is stopped and then beam extraction control is stopped (step 813). After this, the irradiation controller 44 confirms whether the irradiation inside the layer is completed (step 814). If the irradiation inside the layer is not completed, a starting position of the beam irradiation is changed (step 815) and beam control is continued. The irradiation controller 44 determines whether next irradiation data exists (step 816). If the next irradiation data does not exist, the irradiation controller 44 outputs the irradiation completion signal 445 to the interlock system 60. The interlock system 60 then outputs the irradiation completion command 612 to the timing system 50. The timing system 50 outputs the deceleration control startup timing signal 513, and the power supply controller 45 selects the deceleration control data corresponding to the present extraction energy (step 821) and after executing deceleration control (step 822), completes irradiation control (step 823).

Conversely if the next irradiation data exists, the irradiation controller 44, after updating a target energy level in step 817, uses stored-beam quantity detection means 15 to measure in step 818 the amount of beam charge 151 stored within the synchrotron and determine in step 819 whether the amount of stored beam charge 151 suffices for the irradiation with the beam of the next energy level. If the amount of stored beam charge 151 suffices for the next beam irradiation, the irradiation controller 44 outputs the energy change request signal 443 to the interlock system 60. The interlock system 60 then outputs the energy change command 611 to the timing system 50. The timing system 50 outputs the acceleration control timing signal 511, and the power supply controller 45 selects the acceleration control data corresponding to the present extraction energy and shifts to beam acceleration control for the next irradiation energy level (step 820).

Conversely if the amount of stored beam charge is determined to be insufficient, the irradiation controller 44 outputs the deceleration control request signal 444 to the interlock system 60. The interlock system 60 then outputs the deceleration control command 613 to the timing system 50. The timing system 50 outputs the deceleration control startup timing signal 513, and the power supply controller 45 selects the deceleration control data corresponding to the present extraction energy (step 821) and executes deceleration control (step 822). After deceleration control, the power supply controller 45 updates the operating cycle (step 824) and continues the beam irradiation. Although this is not clearly indicated in the control flow diagram of FIG. 6, if any trouble with the power supply controller 45 and the power supply 46 for each of the constituent devices of the synchrotron occurs during beam extraction control, the status information 452 indicating that either of the elements is abnormal is transmitted from the power supply controller 45 to the interlock system 60. On the basis of the status information 452 indicating the abnormality of the element(s), the interlock system 60 outputs the deceleration control command 613 to the timing system 50 and rapidly executes deceleration control using the deceleration control data corresponding to the present extraction energy.

Examples of control data output during the multi-energy extraction operation characterizing the present embodiment are shown in FIGS. 7A and 7B. FIGS. 7A and 7B show the examples of output that use the operating control data 700 shown in FIG. 3. In the examples, beams of three energy levels, namely Ea, Eb, Ec, can be extracted within one operating cycle. FIG. 7A shows how the excitation current value of each bending magnet will change when extraction control is conducted upon the ion beams of all the three energy levels (Ea, Eb, Ec) within one operating cycle. FIG. 7B shows how the excitation current value of each bending magnet will change when the ion beams of two energy levels (Ea, Eb) are extracted at a first operating cycle and then after a shift to deceleration control has been conducted for a reason such as the exhaustion of the stored ion beam charge, the operating cycle is updated and the ion beam of the remaining energy level (Ec) is extracted at the next operating cycle. In general, the excitation current value of the bending magnet and the beam energy are nearly proportional, so the changes shown in FIGS. 7A and 7B can also be taken to mean the changes that the beam energy exhibit during multi-energy extraction operation.

In addition, in the scanning irradiation method, since the extraction energy of the beam differs according to operating cycle, the beam is first accelerated to its initial energy (Einit) and then the control is shifted to deceleration control to obtain the injection energy (Einj) so that a history of magnetic fields in the deceleration control data shown in the present embodiment will be kept constant.

First, an example of the output that uses multi-energy control is described below using FIG. 7A. Upon the acceleration control timing signal 511 being output from the timing system 50, the power supply controller 45 selects the acceleration control data 71a corresponding to the initial energy level, and starts excitation current data updating control. After acceleration control, the accelerator controller 40 confirms the energy of the orbiting beam 10b and outputs the energy determination signal 402 to the interlock system 60. If the reached energy level agrees with the target energy level (in this case, the reached energy level and the target energy level are both Ea), the interlock system 60 outputs the extraction control command 614 to the timing system 50. The timing system 50 outputs the extraction control timing signal 512 in accordance with the extraction control command 614 from the interlock system 60. In accordance with the extraction control timing signal 512, the power supply controller 45 updates the extraction control data 72a corresponding to the extraction energy level Ea. Concurrently with this, the irradiation controller 44 outputs the extraction control permission signal 441. The application process 74 for the extraction radio-frequency signal is consequently conducted, whereby extraction control of the beam is executed. After the irradiation of the affected region has reached the desired dose as a result of beam extraction control, the irradiation controller 44 turns off the extraction control permission signal 441 to stop the extraction radio-frequency signal application process 74.

After the above, the irradiation controller 44 outputs the energy change request signal 443 to the interlock system 60 according to determination results on whether the next irradiation energy is present, and measurement results on the amount of beam charge stored in the synchrotron 13. The interlock system 60 outputs the energy change command 611 to the timing system 50, and then the timing system 50 outputs the acceleration control timing signal 511 to accelerate the stored beam to the next energy. In accordance with the acceleration control timing signal 511, the power supply controller 45 starts the updating control of the acceleration control data 71b corresponding to the extraction energy level Eb. After beam acceleration based on the acceleration control data 71b, the accelerator controller 40 confirms agreement between the target energy level and the reached energy level as in the case of beam extraction control of the initial extraction energy level Ea, and the power supply controller 45 extracts the beam by use of the extraction control data 72b corresponding to the extraction energy level Eb.

After extracting the beam of the extraction energy level Ec by repeating such control, the irradiation controller 44 confirms absence of next irradiation energy and transmits the irradiation completion signal 445 to the interlock system 60. The interlock system 60 then transmits to the timing system 50 the irradiation completion command 612 indicating that a next operating cycle to be controlled is absent. The timing system 50 outputs the deceleration control startup timing signal 513. The power supply controller 45 shifts to deceleration control in accordance with the deceleration control startup timing signal 513. In deceleration control, the deceleration control data 73c corresponding to the immediately previous extraction energy level Ec is selected and the updating control of the deceleration control data 73c is started. Based on the deceleration control data 73c, deceleration control is conducted to decelerate the beam to the injection energy (Einj) after accelerating the beam to the initial energy (Einit). Thus the history of magnetic fields for each operating cycle is held constant. In timing with the completion of updating of the deceleration control data 73c, the timing system 50 outputs the deceleration completion timing signal 514 to complete the irradiation in accordance with the irradiation completion command 612.

Next, a flow of processing in the case that the operating cycle is updated during multi-energy extraction control, as shown in FIG. 7B, is described below. Reference numbers and symbols shown in the figure denote the same as in FIG. 7A. The following describes the process flow that follows the completion of extraction control of the second energy level Eb shown in FIG. 7B.

After extraction control of the second energy level Eb, the irradiation controller 44 confirms presence of the next irradiation data (step 817) and then measures the amount of beam charge 151 stored within the synchrotron. If a result of the measurement indicates that the amount of beam to be next extracted cannot be satisfied, the irradiation controller 44 transmits the deceleration control request signal 444 to the interlock system 60. The interlock system 60 then outputs the deceleration control command 613 to the timing system 50 in accordance with the deceleration control request signal 444. The timing system 50 outputs the deceleration control startup timing signal 513 in accordance with the deceleration control command 613 that has been input. In accordance with the deceleration control startup timing signal 513, the power supply controller 45 selects the deceleration control data 73b corresponding to the immediately previous extraction energy Eb, and starts the updating control of the deceleration control data 73b.

The timing system 50 outputs the deceleration completion timing signal 514 in timing with the completion of updating of the deceleration control data 73c. After this output, because the next irradiation data is present, the target energy is changed from Eb to Ec, then the operating cycle is updated, and the acceleration control timing signal 511 is output.

The power supply controller 45, upon receiving the acceleration control timing signal 511, starts the updating control of the acceleration control data 71a. After acceleration control, the accelerator controller 40 compares the reached energy level and the target energy level. At this time, the reached energy corresponding to the acceleration control data 71a is Ea, but disagreement in extraction energy may occur (Ea≠Ec) since the target energy is Ec. In this case, the irradiation controller 44 leaves the extraction control permission signal 441 turned off until the target energy level and the reached energy level have agreed. The radio-frequency signal for extraction, therefore, is not applied. The timing system 50, on the other hand, repeatedly outputs the extraction control timing signal 512 and the energy change timing signal 513 until the target energy has been reached. In accordance with the timing signals from the timing system 50, the power supply controller 45 controls the updating of the extraction control data 72a, the acceleration control data 71b, the extraction control 72b, and the acceleration control data 71c, in that order. After accelerating the beam until the reached energy has agreed with the target energy Ec, the irradiation controller 44 outputs the extraction control permission signal 441. As a result, the application process 74 for the extraction radio-frequency signal is conducted, whereby the beam is then extracted. After beam extraction control, the irradiation controller 44 confirms whether next irradiation data is present. In the present embodiment, since the next irradiation data is absent (Ec is final energy), the irradiation controller 44 transmits the irradiation completion signal 445 to the interlock system 60. The interlock system 60 transmits to the timing system 50 the irradiation completion command 612 indicating that a next operating cycle to be controlled is absent. The timing system 50 outputs the deceleration control startup timing signal 513. The power supply controller 45 shifts to deceleration control in accordance with the deceleration control startup timing signal 513. In deceleration control, the deceleration control data 73c corresponding to the immediately previous extraction energy level Ec is selected and the updating control of the deceleration control data 73c is started. Based on the deceleration control data 73c, deceleration control is conducted to decelerate the beam to the injection energy (Einj) after accelerating the beam to the initial energy (Einit). Thus the history of magnetic fields for each operating cycle is held constant. In timing with the completion of updating of the deceleration control data 73c, the timing system 50 outputs the deceleration completion timing signal 514 to complete the irradiation in accordance with the irradiation completion command 612.

The above configuration of the irradiation system according to the present embodiment enables the system to rapidly achieve controlling the energy changes of the extraction beam in the synchrotron and updating the operating cycle in the case of ion beam irradiation being halted, and hence to improve the dose rate.

In addition, since the plurality of extraction control sections 72a to 72c of the pattern data 70 for multi-energy extraction control comprise data that correspond only to the energy levels required for treatment of each patient, a wasteful time that is not contributing to beam irradiation (i.e., the control time from the incident beam energy to the irradiation starting energy and the control time from the irradiation ending energy to the deceleration ending energy) is prevented to occur. Accordingly, the beam irradiation in a desired energy range is achieved at a short operating cycle and the dose rate is enhanced.

Second Embodiment

A second embodiment of the present invention is described below using FIGS. 9 to 13A and 13B.

First, a control data structure for the multi-energy extraction operation characterizing the present embodiment, and an operation sequence using the control data are described below using FIGS. 9 to 13A and 13B.

Figure 9:
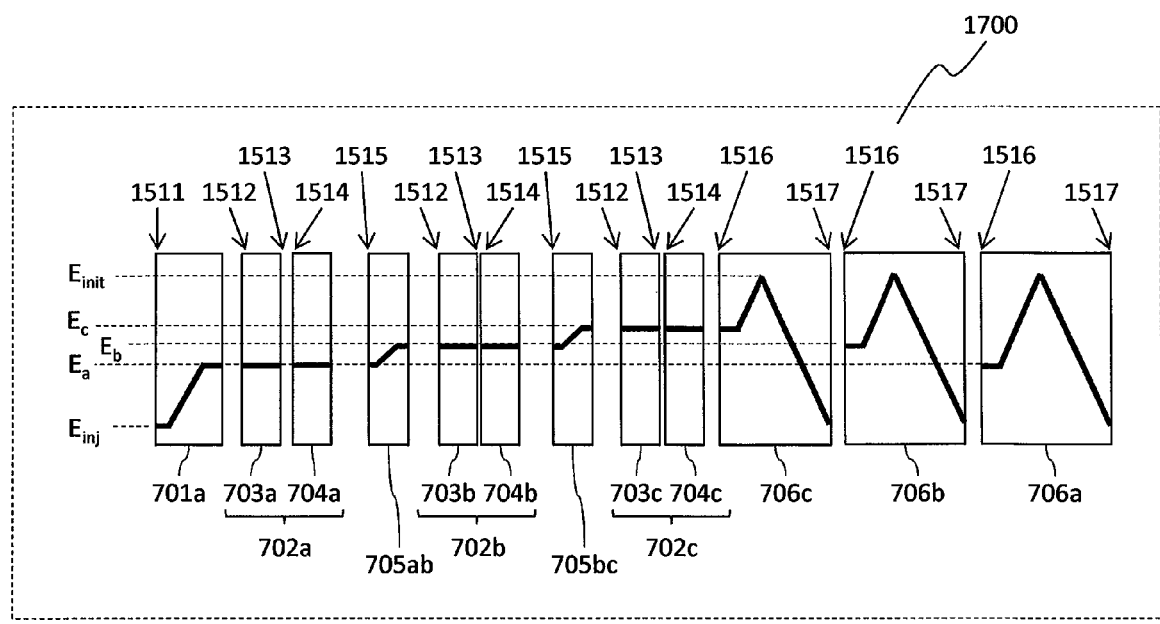
FIG. 9 is a diagram that shows composition of control data relating to a plurality of devices that constitute a synchrotron in a second embodiment of the present invention.

FIG. 9 is a diagram that shows composition of operating control data relating to the devices constituting the synchrotron, the diagram also showing the excitation current of the bending magnets 18 as a typical example of the operating control data relating to the devices of the synchrotron. In actuality, as shown in Non-Patent Document 2, data of the number of levels corresponding to the number of energy levels of the beams to be irradiated is provided, but the data described in the present embodiment is of three levels. In addition, while the operating control data that gives rise to sequential beam irradiation from lower energy levels to higher ones is shown in the present embodiment, substantially the same effects can also be obtained from sequential beam irradiation from higher energy levels to lower ones.

Figure 10:
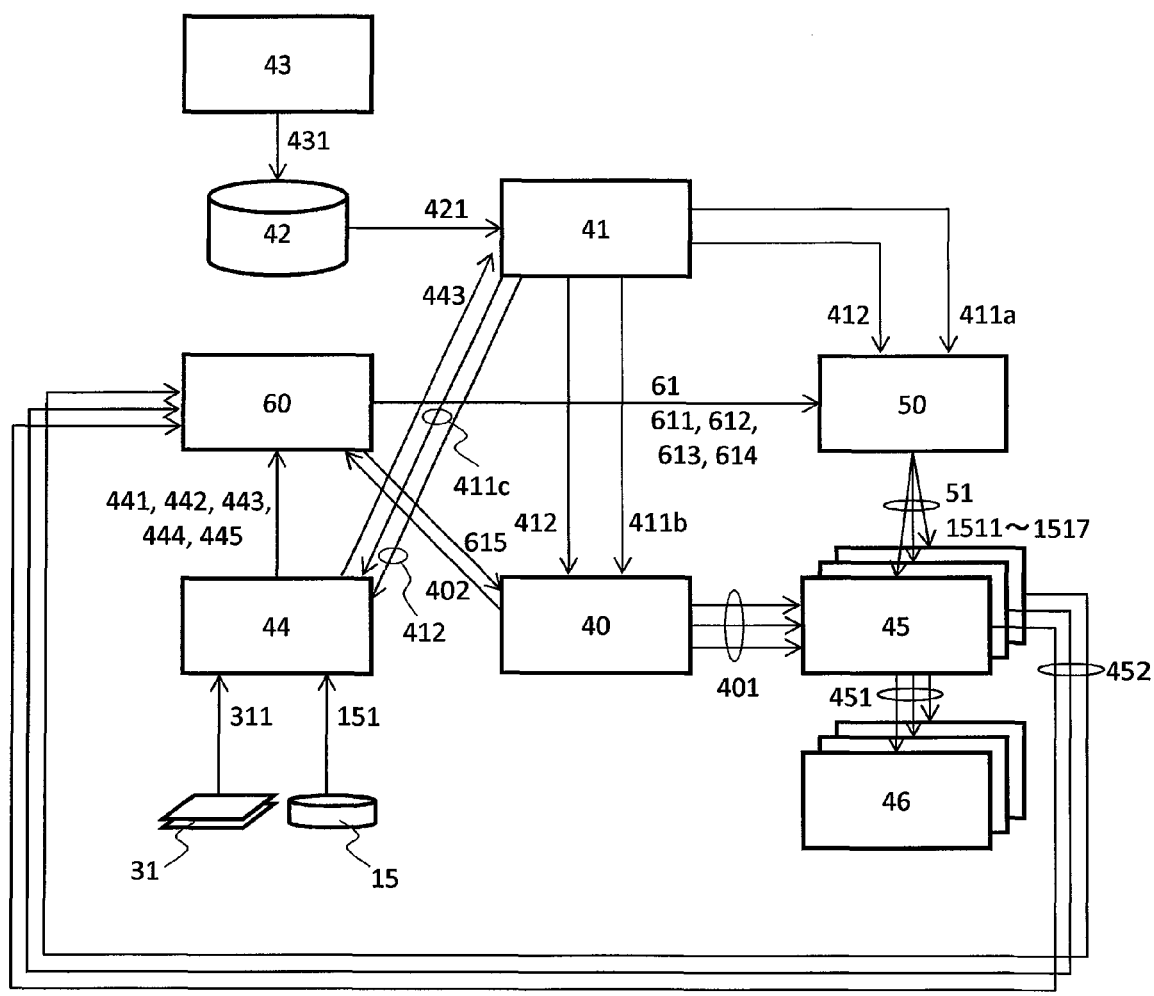
FIG. 10 is a diagram that shows a configuration of a control system (controllers) for realizing multi-energy extraction operation in the second embodiment of the present invention, the diagram also showing information transmission between the devices.
Figure 11:
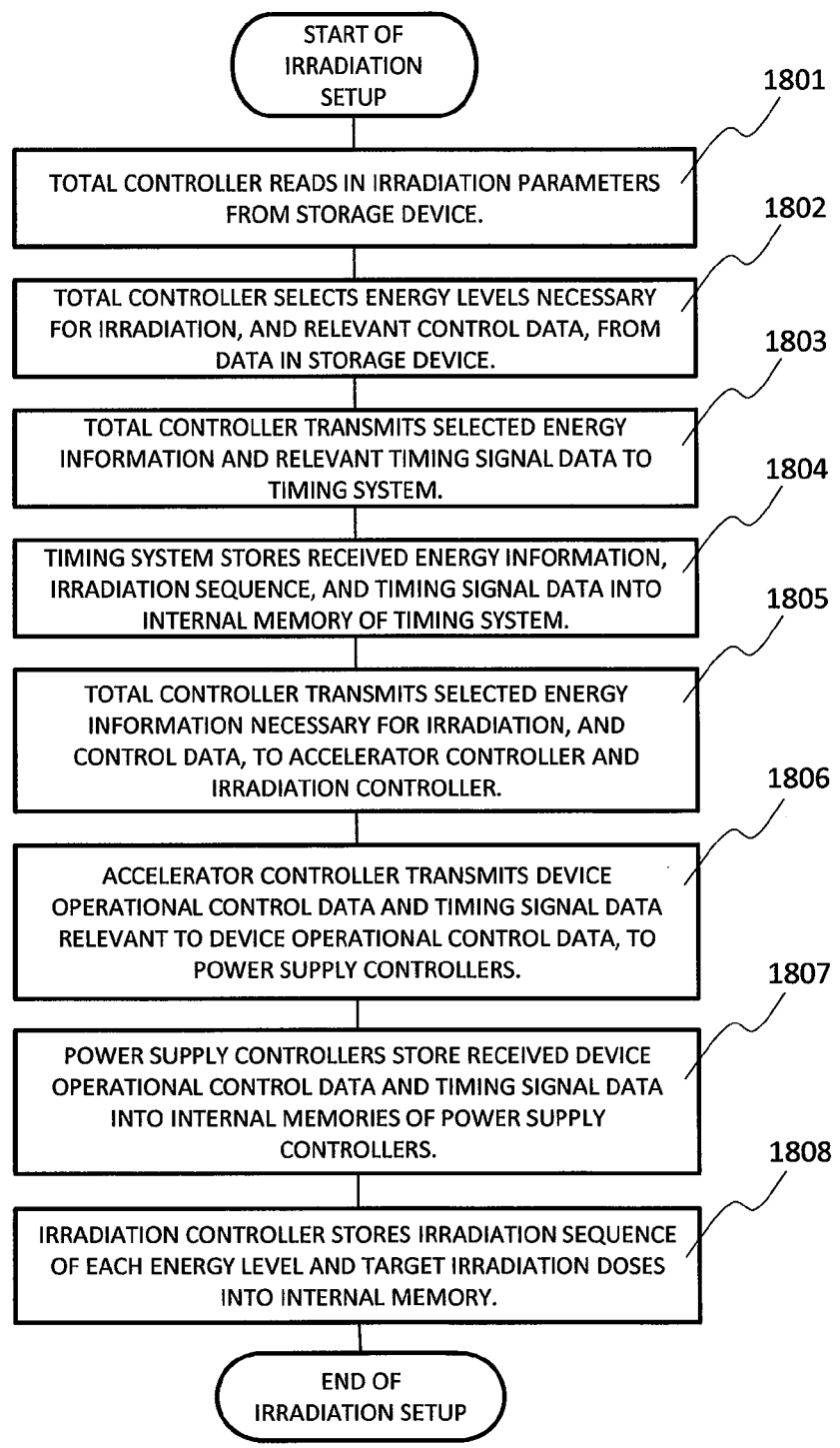
FIG. 11 is a diagram showing a flow of irradiation setup conducted before multi-energy extraction operation is started in the second embodiment of the present invention.
Figure 12:
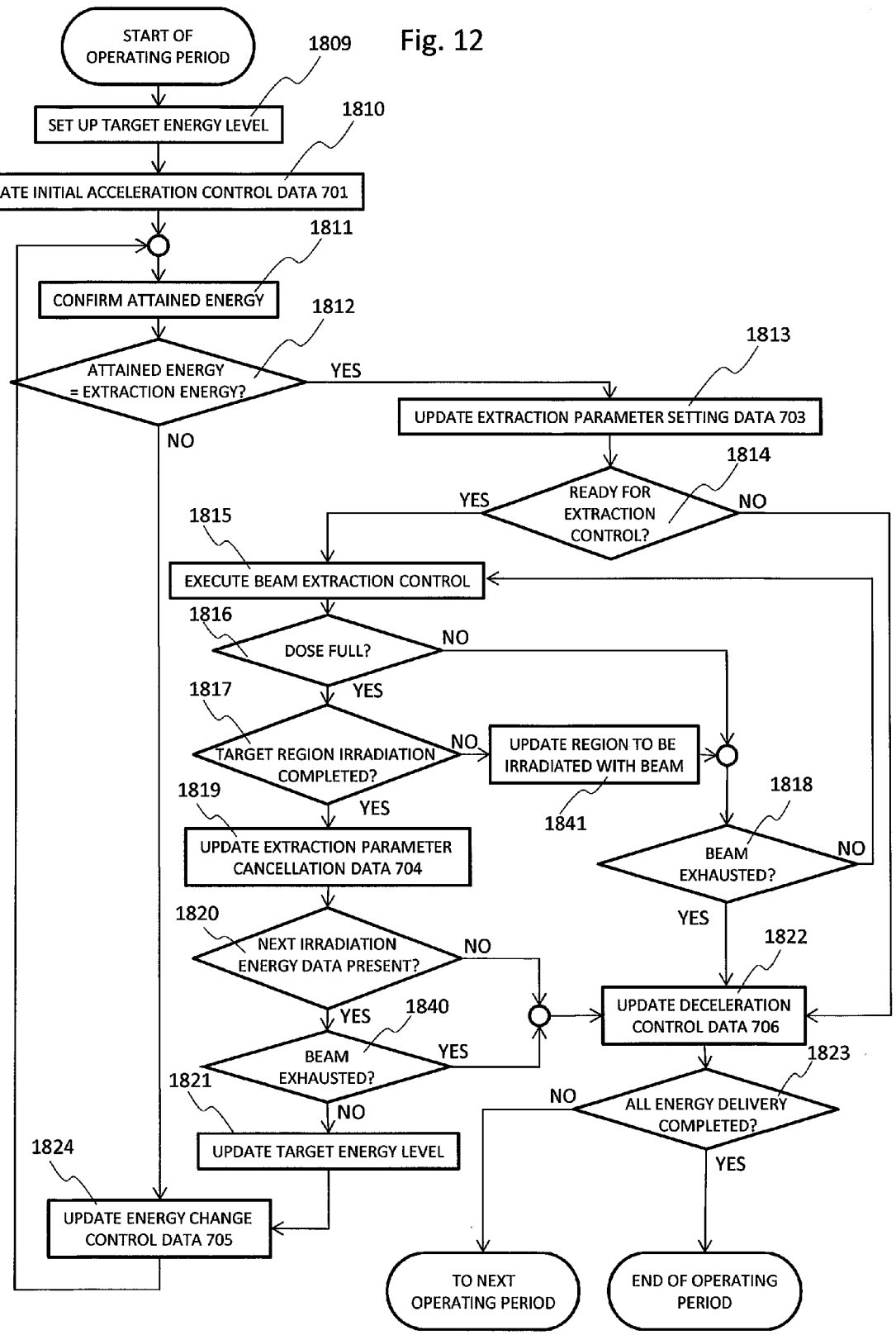
FIG. 12 is a diagram showing a flow of control for multi-energy extraction operation in the second embodiment of the present invention.
Figure 13A:
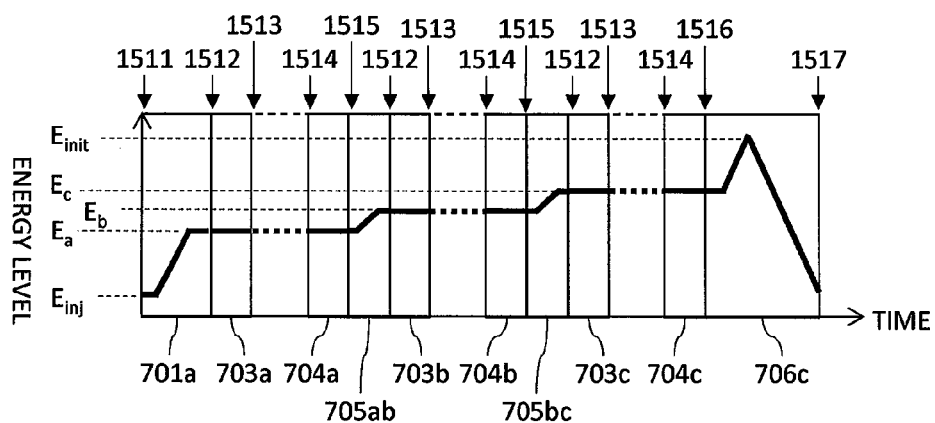
FIG. 13A is a diagram showing an example of control data output during multi-energy extraction operation in the second embodiment of the present invention, the multi-energy extraction operation being based on a combination of the control data shown in FIG. 9.
Figure 13B:
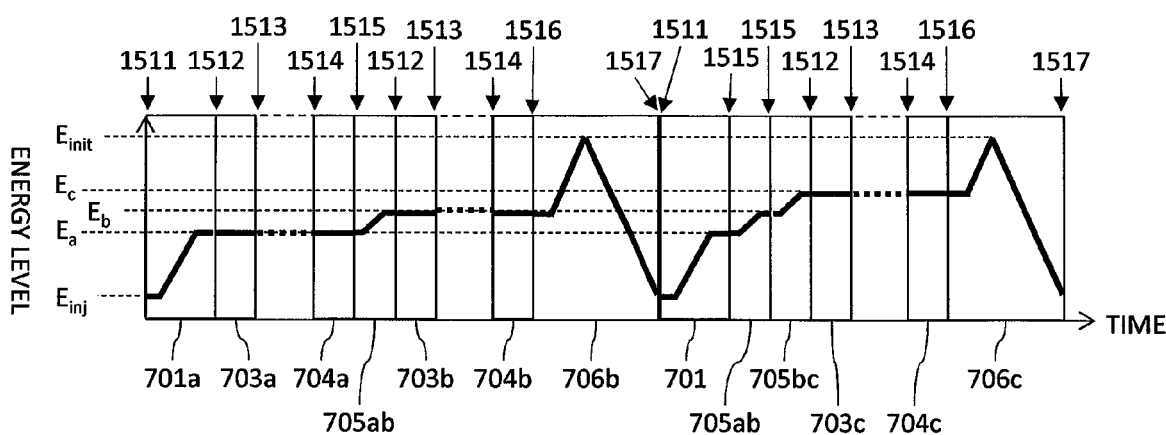
FIG. 13B is a diagram showing another example of control data output during multi-energy extraction operation in the second embodiment of the present invention, the multi-energy extraction operation being based on another combination of the control data shown in FIG. 9.

FIG. 10 is a diagram showing a configuration of a control system 100 (controllers) for achieving the multi-energy extraction operation characterizing the present embodiment. A flow of information transmission between the devices is also shown in FIG. 10. FIG. 11 is a diagram showing a flow of irradiation setup conducted before multi-energy extraction operation is started. FIG. 12 is a diagram showing a flow of control for the multi-energy extraction operation. FIGS. 13A and 13B show examples of control data output during the multi-energy extraction control based on combinations of the control data shown in FIG. 9.

As shown in FIG. 9, operating control data 1700 on the plurality of devices constituting the synchrotron (in the shown example, operating control data on the bending magnets 18) includes the following: initial acceleration control data 701a (hereinafter, represented by 701); a plurality of sets of extraction control data, 702a to 702c, for extracting beams of a plurality of energy levels (in the shown example, three energy levels, Ea, Eb, Ec), the extraction control data sets being hereinafter represented by 702; a plurality of sets of energy change control data, 705ab to 705bc, for connecting the plurality of sets of extraction control data 702, the energy change control data sets being hereinafter represented by 705; and a plurality of sets of deceleration control data, 706a to 706c (hereinafter, represented by 706), that correspond to the plurality of sets of extraction control data 702.

The extraction control data 702 includes a plurality of sets of extraction parameter setting data, 703a to 703c, hereinafter represented by 703) and a plurality of sets of extraction parameter cancellation data, 704*a* to 704*c*, hereinafter represented by 704. Combining these sets of control data allows extraction control of the beams of the plurality of energy levels. Additionally, the presence of the deceleration control data 706 corresponding to the beams of the plurality of energy levels allows rapid shifting to deceleration control from whatever extraction energy level. The control data sets are each provided as time-series data on a current/voltage which is a control quantity assigned directly to the relevant device. The control data relating to the bending magnets 18, for example, includes time-series data on the excitation current and voltage (not shown) that are set up for the bending magnet power supply 46B needed to generate predetermined bending magnetic field strength. The control data may include the time-series data relating to the bending magnetic field strength, and the time-series data relating to the bending magnetic field strength may be converted into the control quantity (current/voltage) assigned directly to the device during control.

The control data is stored in the storage device 42. Including the control data shown in FIG. 9, control data that enables the extraction of the beams of all energy levels corresponding to irradiation parameters for all patients assumed is stored as module data in the storage device 42. For example, if the number of extraction energy levels corresponding to the irradiation parameters for the plurality of patients assumed is 100, then 100 sets of initial acceleration control data, 701, 100 sets of extraction control data, 702, 99 sets of energy change control data, 705, and 100 sets of deceleration control data, 706, are stored as module data in the storage device 42. During irradiation setup, when the irradiation parameters for a specific patient are assigned, the total controller 41 selects the corresponding data from the control data stored within the storage device 42, and stores the selected data into the power supply controller 45. The module data that enables the extraction of the beams of all energy levels may be stored into an internal storage device of the total controller 41.

The control data sets in the operating control data 1700 are associated with respective timing signals 51 that are output from the timing system 50. The timing signals 51 in the present embodiment include an acceleration control startup timing signal 1511, an extraction parameter setting timing signal 1512, an extraction control stand-by timing signal 1513, an extraction parameter cancellation timing signal 1514, an energy change control timing signal 1515, a deceleration control startup timing signal 1516, and a deceleration control completion timing signal 1517. Upon input of one such timing signal 51 to the power supply controller 45, the power supply controller 45 selects the control data set associated with the timing signal 51, and starts data updating from an initial address of the selected control data set.

The updating control of the operating control data 1700 in response to the input of the timing signal 51 is described below using FIG. 9. The power supply controller 45, upon receiving the acceleration control timing signal 1511, updates the initial acceleration control data 701 from injection energy (Einj) to extraction energy (Ea) of an initial level and accelerates the beam. After receiving the acceleration control timing signal 1512, the power supply controller 45 updates the extraction parameter setting data 703*a*. The updating of the extraction parameter setting data 703*a* is stopped upon input of the extraction control stand-by timing signal 1513. The accelerator controller 40 applies an extraction radio-frequency voltage to the extraction radio-frequency electrodes 20*a*, to conduct beam extraction control. The irradiation controller 44 sequentially measures the irradiation dose 311 occurring during extraction control, then outputs a full dose signal 442 in accordance with the measured value, and stops the application of the extraction radio-frequency voltage to complete extraction control. After this, input of the extraction parameter cancellation timing signal 1514 starts the updating of the extraction parameter cancellation data 704*a*. Depending on the amount of stored beam charge existing at the completion of extraction control and on whether next irradiation energy is present, the timing system 50 determines whether the energy change timing signal 1515 is outputted to shift to energy change control (i.e., shift from the extraction parameter cancellation data 704*a* to the energy change control data 705*ab*) or the deceleration control timing signal 1516 is outputted to shift to deceleration control (i.e., shift from the extraction parameter cancellation data 704*a* to the deceleration control data 706*a*). An ending value of the extraction parameter cancellation data 704 and a starting value of the energy change control data 705 for shifting the beam to the next irradiation energy level (e.g., an ending value of 704*a* in FIG. 9 and a starting value of 705*ab* in the figure) are set to be the same value in the operating control data 1700 so that both values can be continuously connected. The same also applies for the ending value of the extraction parameter cancellation data 704 and a starting value of the deceleration control data for decelerating the beam to injection energy (e.g., the ending value of 704*a* in FIG. 9 and a starting value of 706*a* in the figure). By realizing such operating control based on the input of the timing signal 51, the control data can be easily changed and updated according to the input of the timing signal 51.

In addition, when the multi-energy extraction operation described above is executed, the interlock system 60 outputs an interlock signal 61 based on an energy determination signal 402 outputted from the accelerator controller 40, an energy change request signal 443, a deceleration control request signal 444, and an irradiation completion signal 445, each output from the irradiation controller 44, and on status information 452, output from the power supply controller 45, to indicate whether the relevant devices are sound. The interlock signal 61 includes an energy change command 611, an extraction control command 614, an irradiation completion command 612, and a deceleration control command 613. The timing system 50 outputs the energy change timing signal 1515 in accordance with the energy change command 611 output from the interlock system 60. The timing system 50 also outputs the extraction parameter setting timing signal 1512 in accordance with the extraction control command 614 output from the interlock system 60. In addition, the timing system 50 outputs the extraction parameter cancellation timing signal 1514 in accordance with the irradiation completion command 612 output from the interlock system 60. The timing system 50 further outputs the deceleration control startup timing signal 1516 in accordance with the deceleration control command 613.

A flow of irradiation setup for executing multi-energy extraction control using the control data shown in FIG. 9 for the devices constituting the synchrotron is described below using FIGS. 10 and 11 together.

First, the treatment planning device 43 registers treatment planning information 431, containing the irradiation parameters and others required for the treatment of the patient, in the storage device 42. In step 1801, on the basis of the setting information of the irradiation parameters, the total controller 41 reads in the irradiation parameters 421 from the storage device 42. In step 1802, using the irradiation parameters 421, the total controller 41 selects the energy information necessary for irradiation, target irradiation doses, an irradiation sequence and control data, from the storage device 42. As described above, in the storage device 42, the control data including the initial acceleration control data 701, extraction control data 702, extraction parameter setting data 703, extraction parameter cancellation data 704, energy change control data 705, and deceleration control data 706 shown in FIG. 9 and enabling the extraction of the beams of all energy levels corresponding to the irradiation parameters for all patients assumed is stored as the module data. The total controller 41 selects and reads in the control data set 701-706 in accordance with the irradiation parameters 421.

In step 1803, the total controller 41 transmits control data 411a including the energy information necessary for irradiation, the irradiation sequence and timing signals corresponding to the energy information, to the timing system 50.

In step 1804, the timing system 50 stores the control data 411a including the energy information necessary for irradiation, irradiation sequence and timing signals corresponding to the energy information, that have been transmitted from the total controller 41, into an internal memory of the timing system 50. In step 1805, the total controller 41 likewise transmits control data sets 411b, 411c including the energy information necessary for irradiation, the irradiation sequence and the operating control data (control data sets 701-706) for each device corresponding the energy information and timing signals (timing signals 1511-1517) corresponding to the operating control data, to the accelerator controller 40 and the irradiation controller 44. The control data set 411b transmitted to the accelerator controller 40 includes the operating control data (control data sets 701-706) for each device and timing signals (timing signals 1511-1517) corresponding to the operating control data. The control data set 411c transmitted to the irradiation controller 44 includes the irradiation sequence of each irradiation energy level and target irradiation doses.

In step 1806, the accelerator controller 40 transmits control data 401 to each power supply controller 45 for each of the constituent devices of the synchrotron 13 and beam transport apparatus 14, the control data 401 including the operating control data (control data sets 701-706) for each device and timing signals (timing signals 1511-1517) corresponding to the operating control data. In step 1807, the power supply controller 45 stores the control data 401 into an internal memory of the controller 45. In step 1808, the irradiation controller 44 stores the irradiation sequence of irradiation energy levels and the target irradiation doses into an internal memory of the controller 44.

Next, a flow of the irradiation conducted when multi-energy extraction control is executed using the control data (shown in FIG. 9) that relates to the devices constituting the synchrotron is described below using FIGS. 10 and 12.

Upon input of an irradiation starting command (not shown) from a user, the total controller 41 starts operating control of the synchrotron 13. The total controller 41 outputs to the timing system 50, the accelerator controller 40, and the irradiation controller 44, a control starting command 412 indicating a start of the operating cycle of the synchrotron 13. In step 1809, the timing system 50, the accelerator controller 40, and the irradiation controller 44 sets up a target energy level in accordance with the control starting command 412. In accordance with the target energy level that has been set up, the timing system 50 sets up target energy information for the beam which is to be extracted, and the accelerator controller 40 sets the target energy level in each power supply controller. The irradiation controller 44 sets up from the target energy level a target dose value in each of doses management regions for the energy level.

In step 1810, the timing system 50 outputs the acceleration control startup timing signal 1511 in accordance with the control starting command, and the power supply controller 45 starts updating the initial acceleration control data 701. In step 1811, upon completion of initial acceleration control, the accelerator controller 40 confirms the energy level that has been reached after the acceleration, and in step 1812, determines whether the reached energy level confirmed after the acceleration agrees with the target energy level. If the operating cycle is updated after the deceleration control described later, the reached energy level upon completion of initial acceleration control will differ from the next extraction target energy level, so the above determination is conducted to determine whether control is to be shifted to the energy change control described later, or directly shifted to beam extraction control.

The accelerator controller 40 outputs to the interlock system 60 the energy determination signal 402 denoting a result of the energy determination. If the reached energy level upon completion of initial acceleration control disagrees with the extraction energy level, the interlock system 60 outputs the energy change command 611 to the timing system 50, then the timing system 50 outputs the energy change control timing signal 1515 to the power supply controller 45, and the power supply controller 45 updates the energy change control data 705 (step 1823). If the reached energy level upon completion of initial acceleration control agrees with the extraction energy level, the interlock system 60 outputs the extraction control command 614 to the timing system 50, then the timing system 50 outputs the extraction parameter setting timing signal 1512 to the power supply controller 45, and the power supply controller 45 updates the extraction parameter setting data 703 (step 1813).

The timing system 50 outputs the extraction control standby timing signal 1513 in timing with completion of the updating of the extraction parameter setting data 703, terminates the updating of the extraction parameter setting data 703 that is taking place in the power supply controller 45, and holds final updated data value. The interlock system 60 determines whether the extraction control of the beam can be conducted (step 1814). This determination is based on the status information 452, the extraction control permission signal 441, etc., the status information 452 being output from the power supply controller 45 and including the energy confirmation information and other information to indicate whether the relevant devices are sound, and the extraction control permission signal 441 being output from the irradiation controller 44 based on the stored-beam quantity value 151 measured by the stored-beam quantity detection means 15 inside the synchrotron 13.

If a result of the determination is 'No', the interlock system 60 outputs the deceleration control command 613 to the timing system 50. The timing system 50 outputs the deceleration control startup timing signal 1516 to the power supply controller 45. The power supply controller 45 updates the deceleration control data 706 (step 1822).

If the result of the determination is 'Yes', the interlock system 60 outputs the extraction permission signal 615 to the accelerator controller 40. The accelerator controller 40 applies the extraction radio-frequency voltage to the radio-frequency electrodes 20a and executes beam extraction control (step 1815).

During beam extraction control, the dose monitor 31 within the irradiation apparatus 30 sequentially measures the irradiation dose 311 of the beam, and the irradiation controller 44 computes a total dose that has been integrated in the doses management region. At this time, the irradiation controller 44 compares the target dose and total dose in the doses management region and determines whether the total dose has reached the target dose (step 1816).

If the total dose in the doses management region is smaller than the target value, uses the stored-beam quantity detection means 15 measures the amount of synchrotron-stored beam charge 151, and the irradiation controller 44 determines whether a sufficient amount of beam for continued beam irradiation is stored (step 1818). Beam irradiation is continued if a sufficient amount of beam for continued beam irradiation is stored. Conversely if the beam charge stored in the synchrotron 13 is exhausted, the irradiation controller 44 outputs the deceleration control request signal 444 to the interlock system 60. The interlock system 60 then outputs the deceleration control command 613 to the timing system 50. The timing system 50 outputs the deceleration control startup timing signal 1516 to the power supply controller 45. The power supply controller 45 updates the deceleration control data 706 (step 1822).

If the total dose in the doses management region equals the target value, the irradiation controller 44 determines whether the irradiation is completed in the irradiation target region of the energy, that is, in the management region of all doses corresponding to the energy (step 1817).

If the irradiation in the management region of all doses corresponding to the energy is not completed, the irradiating position is updated to a beam irradiation region in which the irradiation using the scanning magnets 32 is not yet completed, that is, to a doses management region in which the irradiation is not yet completed (step 1841). After that, as in the case that the target dose is not reached in step 1816, the irradiation controller 44 determines whether a sufficient amount of beam charge for continued beam irradiation is stored (step 1818). Beam irradiation is continued if a sufficient amount of beam for continued beam irradiation is stored. If the beam charge stored in the synchrotron 13 is exhausted, the irradiation controller 44 outputs the deceleration control request 444 to the interlock system 60. Conversely if the irradiation in the management region of all doses corresponding to the energy has been completed, the irradiation controller 44 outputs the irradiation completion signal 445 to the interlock system 60. The interlock system 60 outputs the irradiation completion command 612 to the timing system 50. The timing system 50 outputs the extraction parameter cancellation timing signal 1514 to the power supply controller 45, and the power supply controller 45 then starts updating the extraction parameter cancellation data 704 (step 1819).

After the updating control of the extraction parameter cancellation data 704, the irradiation controller 44 determines whether next target energy data is present (step 1820). If the next target energy data is present, uses the stored-beam quantity detection means 15 measures the amount of synchrotron-stored beam charge 151, and the irradiation controller 44 determines whether a sufficient amount of beam for irradiation with the next target energy is stored (step 1840). If a sufficient amount of beam for the irradiation with the next target energy is stored, the irradiation controller 44 updates the target energy data (step 1821). Conversely if the beam charge stored in the synchrotron 13 is exhausted, the irradiation controller 44 outputs the deceleration control request 444 to the interlock system 60. The interlock system 60 outputs the deceleration control command 613 to the timing system 50. The timing system 50 then outputs the deceleration control startup timing signal 1516 to the power supply controller 45. The power supply controller 45 updates the deceleration control data 706 (step 1822). In a case that the irradiation region for managing doses is finely specified as in the spot-scanning irradiation method, the stored-beam quantity determination described in step 1840 may be skipped and as shown in step 1818, the amount of stored beam charge may be sequentially determined. This enables the appropriate irradiation. To perform in-layer irradiation with a uniform continuous beam as in raster scanning irradiation, it is desirable that for enhanced dose rate and for ease in securing the uniformity of the irradiation dose, the irradiation be controlled to prevent beam exhaustion during the irradiation process. As shown in FIG. 12, the determination process in step 1840 for determining whether a sufficient amount of beam for the beam irradiation with the next target energy is stored is provided in front of the process for updating the target energy data.

If a sufficient amount of beam for the beam irradiation is stored in the synchrotron 13, the irradiation controller 44 updates the target energy data and then outputs the energy change request 443 to the interlock system 60. The interlock system 60 outputs the energy change command 611 to the timing system 50. The timing system 50 outputs the energy change control timing signal 1515 to the power supply controller 45. The power supply controller 45 updates the energy change control data 705 in accordance with the energy change control timing signal 1515 (step 1824).

Conversely if the next target energy data is absent, that is, if the irradiation with the beams of all energy levels is already completed, the irradiation controller 44 outputs the deceleration control request 444 to the interlock system 60. The interlock system 60 outputs the deceleration control command 613 to the timing system 50. The timing system 50 outputs the deceleration control startup timing signal 1516 to the power supply controller 45. The power supply controller 45 updates the deceleration control data 706 (step 1822).

The timing system 50 outputs the deceleration control completion timing signal 1517 in timing with completion of the updating of the deceleration control setting data. In accordance with input of the deceleration control completion timing signal 1517, the interlock system 60 confirms whether the irradiation with the beams of all energy levels has been completed (step 1823). The operating cycle is terminated if the irradiation with the beams of all energy levels is already completed.

If the irradiation with the beams of all energy levels is not completed and the control is shifted to deceleration control (step 1823), the sequence returns to the start of the operating cycle and initial acceleration control is restarted.

If the sequence returns to the start of the operating cycle and initial acceleration control is to be restarted, the reached energy level on initial acceleration control will differ from the target energy required for the next irradiation, so the updating control of the energy change control data will be continued until the reached energy agrees with the target energy (i.e., the process flow of steps 1812, 1824, 1811, 1812 in FIG. 12 will be repeated in that order). When the reached energy agrees with the target energy as a result, the control shifts to the updating control of the extraction parameter setting data 703 (step 1813).

Examples of control data output during the multi-energy extraction operation characterizing the present embodiment are shown in FIGS. 13A and 13B. FIGS. 13A and 13B show the examples of output that use the operating control data 1700 shown in FIG. 9. In the examples, beams of three energy levels, namely Ea, Eb, Ec, can be extracted within one operating cycle. FIG. 13A shows how the excitation current value of each bending magnet will change when extraction control is conducted upon the ion beams of all the three energy levels (Ea, Eb, Ec) within one operating cycle. FIG. 13B shows how the excitation current value of each bending magnet will change when the ion beams of two energy levels (Ea, Eb) are extracted at a first operating cycle and then after a shift to deceleration control has been conducted for a reason such as the exhaustion of the ion beam charge, the operating cycle is updated and the ion beam of the remaining energy level (Ec) is extracted at the next operating cycle. In general, the excitation current value of the bending magnet and the beam energy are nearly proportional, so the changes shown in FIGS. 13A and 13B can also be taken to mean the changes that the beam energy exhibit during multi-energy extraction operation.

In common between FIGS. 13A and 13B, the timing signals 1511 to 1517 corresponding to the control data sets 701 to 706 are set and these control data sets are updated in timing with input of the timing signals 1511 to 1517.

First, an example of control data output during multi-energy extraction operation is described below using FIG. 13A. The power supply controller 45 upon receiving the acceleration control timing signal 1511 from the timing system 50 selects initial acceleration control data 701 and starts excitation current data updating control. Upon completion of initial acceleration control, the timing system 50 outputs the extraction parameter setting timing signal 1512 to the power supply controller 45. The power supply controller 45 outputs extraction parameter setting data 703a corresponding to initial extraction energy level Ea. After this, upon receiving the extraction control stand-by timing signal 1513 the power supply controller 45 holds final update value to execute extraction control. Upon completion of extraction control, the timing system 50 outputs the extraction parameter cancellation timing signal 1514 to the power supply controller 45, thus causing the power supply controller 45 to start output of update of extraction parameter cancellation data 704a.

The amount of beam charge stored within the synchrotron 13 is measured synchronously with completion of the update control of the extraction parameter cancellation data 704a. After confirming that the stored beam charge satisfies the amount of beam extraction corresponding to the next energy level, the timing system 50 outputs the energy change control timing signal 1515. The power supply controller 45 selects the energy change control data 705ab that connects the present extraction energy Ea and the next extraction energy Eb, and starts output of update of the control data. Hereafter, the above-described extraction parameter setting control, extraction control, extraction parameter cancellation control, and energy change control are repeated until extraction control of final energy Ec has been completed.

After updating control of the extraction parameter cancellation data 704c relating to the final energy Ec, the timing system 50 outputs the deceleration control startup timing signal 1516. Upon receiving the deceleration control startup timing signal 1516, the power supply controller 45 selects the deceleration control data 706c corresponding to the immediately previous extraction parameter cancellation data 704c, and starts the updating control of the deceleration control data. In deceleration control in the present embodiment, since beam is controlled to be extracted from lower energy levels to higher ones (Ea<Eb<Ec), initial excitation to maximum energy (Einit) is conducted by deceleration control.

The timing system 50 outputs the deceleration control completion timing signal 1517 in timing with completion of deceleration control, and confirms whether extraction control of the beams of all energy levels is completed. If extraction control of the beams of all energy levels is completed, the operating cycle of the synchrotron comes to an end.

Next, a flow of processing in a case that the operating cycle is updated during multi-energy extraction control, as shown in FIG. 13B, is described below. Reference numbers and symbols shown in the figure denote the same as in FIG. 13A. The following describes the process flow that follows completion of the extraction control of the second energy level Eb shown in FIG. 13B.

The amount of beam charge stored within the synchrotron is measured upon completion of the extraction control of the second energy level Eb. If a result of the measurement indicates that the amount of beam to be next extracted cannot be satisfied for a reason such as the exhaustion of the beam, the timing system 50 outputs the deceleration control startup timing signal 1516 corresponding to the energy whose extraction control has been completed. In accordance with the received deceleration control startup timing signal 1516, the power supply controller 45 starts the updating control of the deceleration control data 706b continuously connectible to the immediately previous extraction parameter cancellation data 704b.

Whether the extraction control of the beams of all energy levels is completed is confirmed in timing with input of the deceleration control completion timing signal 1517. If the extraction control of the beams of all energy levels is not completed, the target energy level is changed from Eb to Ec and then the acceleration control timing signal 1511 is output.

The updating of the initial acceleration control data 701 is started upon input of the acceleration control timing signal 1511. After initial acceleration control, a comparison between the reached energy level and the target energy level is conducted. After this comparison, the energy change control timing signal 1515 is output since the reached energy level in the initial acceleration control data 701 is Ea and the target energy level is Ec. The power supply controller 45 updates the energy change data 705ab in accordance with the energy change control timing signal 1515, and executes energy change control. After energy change control, a comparison between the reached energy level and the target energy level is conducted once again. After this comparison, the energy change control timing signal 1515 is output again since the reached energy level after energy change control is Eb and the target energy level is Ec. The energy change data 705bc is updated. This control sequence is repeated so that the reached energy will be accelerated to Ec, the same level as the target energy level. Thereafter, the same control as the extraction control and deceleration control described above is performed.

As described above, in the multi-energy extraction control operation that achieves rapid control of the energy level changes to the beams extracted from the synchrotron in the present embodiment, the control data sets 701-706 include the deceleration control data set 706 corresponding to the plurality of energy levels. This enables rapid shifting to deceleration control from whatever energy level, and if the beam charge stored within the synchrotron becomes insufficient and ion beam irradiation comes to a halt, the operating cycle is updated within a short time. In addition, the dose rate is enhanced and a treatment time is reduced.

Furthermore, even if a constituent device of the particle beam irradiation system encounters trouble and ion beam irradiation comes to a halt, the control can be directly shifted from the extraction energy to deceleration control and the operating cycle can be updated within a short time and safely.

In addition to the above, the plurality of extraction control data sets, 702a to 702c, are applied as the data corresponding only to the energy levels required for the treatment of each patient, which leads to preventing occurrence of a wasteful time not contributing to beam irradiation. More specifically, such application prevents occurrence of both a control time during shifting from the incident beam energy to the irradiation starting energy in the synchrotron, and a control time during shifting from the irradiation ending energy to the deceleration ending energy in the synchrotron. The beam irradiation in a desired energy range is therefore achieved at a short operating cycle and the dose rate is enhanced.

Furthermore, after termination of deceleration control due to beam exhaustion or occurrence of other factors causing a beam irradiation halt, if beam energy not consumed for irradiation is present and the operating cycle is updated, the reached energy level after initial acceleration control or after energy change control might disagree with the next target energy level, the updating control of the extraction control data (i.e., extraction parameter setting control and extraction parameter cancellation control) will be skipped, and energy change control will be immediately executed to accelerate the beam from the reached energy level to the target energy level. Energy change control will therefore be achieved within a short time. In addition, the dose rate will be enhanced and the treatment time reduced.

Furthermore, since the control data sets 701-706 that make up operating control data includes the time-series data relating to the current/voltage which is the control quantity assigned directly to the devices constituting the synchrotron 13, this composition of the operating control data makes parameter change computation unnecessary and simplifies the system configuration and control means.

Moreover, the control data enabling the extraction of the beams of all energy levels corresponding to the irradiation parameters for all patients assumed is stored in the storage device 42 as module data, and the total controller 41 selects the control data set 701-706 in accordance with the irradiation parameters 421, stores the selected control data set into the power supply controller 45, and constructs the operating control data 1700. This leads to preventing the occurrence of a wasteful time not contributing to beam irradiation. More specifically, such data construction prevents the occurrence of both the control time during shifting from the incident beam energy to the irradiation starting energy in the synchrotron, and the control time during shifting from the irradiation ending energy to the deceleration ending energy in the synchrotron. The beam irradiation in the desired energy range is therefore achieved at a short operating cycle and the dose rate is enhanced. The treatment time is also reduced.

What is claimed is:

1. A particle beam irradiation system, comprising:
   a synchrotron constructed to accelerate and extract an ion beam;
   an irradiation apparatus adapted to irradiate the ion beam extracted from the synchrotron; and
   a controller including operating control data to control extraction of beams of a plurality of energy levels in one operating cycle of the synchrotron and to enable rapid shifting to deceleration control from an energy level of the plurality of energy levels, and configured to control devices constituting the synchrotron by using the operating control data,
   wherein the operating control data comprises a plurality of sets of deceleration control data to enable the rapid shifting to deceleration control from an energy level of the plurality of energy levels.

2. The particle beam irradiation system according to claim 1, wherein
   the operating control data includes multi-energy extraction control pattern data corresponding to the beam extraction control of the plurality of energy levels,
   the multi-energy extraction control pattern data including a plurality of acceleration control sections for accelerating the beam to predetermined extraction energy levels and a plurality of extraction control sections for extracting the beam that has been accelerated to the predetermined extraction energy levels,
   the plurality of sets of deceleration control data corresponding to the respective extraction energy levels in the plurality of extraction control sections, and
   the controller is configured to conduct extraction control of the beam of the plurality of energy levels in accordance with the multi-energy extraction control pattern data, and enables a rapid shift to deceleration control from an energy level of the plurality of energy levels by having the plurality of sets of deceleration control data correspond to the respective extraction energy levels in the plurality of extraction control sections.

3. The particle beam irradiation system according to claim 2, wherein
   the plurality of sets of deceleration control data are constructed to have values corresponding to the respective extraction energy levels in the plurality of extraction control sections as initial data values, and to have values corresponding to incident energy level of the synchrotron as final data values.

4. The particle beam irradiation system according to claim 2, wherein
   when the controller shifts from the control of the extraction at a certain energy level to deceleration control, the controller, after completion of updating of currently ongoing control data, selects the deceleration control data corresponding to an immediately previous extraction energy level and shifts to deceleration control.

5. The particle beam irradiation system according to claim 4, wherein
   after completing extraction control of the beam of one of the plurality of energy levels, when a next irradiation data is present, the controller shifts to updating control of a target energy level, and
   when the next irradiation data is absent, the controller shifts to deceleration control.

6. The particle beam irradiation system according to claim 4, wherein
   after completing extraction control of the beam of one of the plurality of energy levels and confirming that a next irradiation data is present, when a stored electrical charge quantity of a beam orbiting inside the synchrotron suffices for executing beam irradiation based upon the next irradiation data, the controller shifts to acceleration control of a next energy level; and when the stored electrical charge quantity of the beam is insufficient for executing the beam irradiation based upon the next irradiation data, the controller shifts to deceleration control.

7. The particle beam irradiation system according to claim 2, wherein
   the multi-energy extraction control pattern data and the plurality of sets of deceleration control data are constituted by time-series data relating to a current/voltage which is a control quantity assigned directly to the devices constituting the synchrotron.

8. The particle beam irradiation system according to claim 2, wherein the controller comprises:
   an irradiation controller configured to manage beam scans and an irradiation dose of the ion beam in the irradiation apparatus;

an interlock system configured to output an interlock signal based upon a status signal on the devices constituting the synchrotron;

a timing system configured to output a control timing signal for total control of operation of the devices constituting the synchrotron; and a power supply controller configured to control each of the devices constituting the synchrotron, wherein the interlock system outputs an energy change command, a deceleration control command, and an irradiation completion command based upon an energy change request signal, deceleration control request signal, and irradiation completion signal, respectively, output from the irradiation controller, wherein the timing system outputs an acceleration control timing signal based upon the energy change command output from the interlock system, and outputs a deceleration control startup timing signal based upon the deceleration control command and the irradiation completion controller, wherein the operating control data is stored in the power supply controller, and wherein the power supply controller conducts updating control of acceleration control data included in the operating control data in response to the acceleration control timing signal, and selects, in response to the deceleration control startup timing signal, the deceleration control data corresponding to an immediately previous extraction energy level from the plurality of sets of deceleration control data and controls updating of the selected deceleration control data.

9. The particle beam irradiation system according to claim 2, wherein the controller comprises:

a storage device in which all data corresponding to irradiation parameters for a plurality of patients assumed is previously stored as the pattern data for multi-energy extraction control; and a power supply controller that controls each of the devices constituting the synchrotron and in which all data corresponding to the irradiation parameters for the plurality of patients assumed is previously stored as the deceleration control data, wherein when irradiation parameters for a specific patient are assigned for irradiation setup, the controller selects multi-energy extraction control pattern data appropriate for the irradiation parameters from the data in the storage device and stores the selected pattern data into the power supply controller, and thereby constructs the operating control data by use of the multi-energy extraction control pattern data and the deceleration control data previously stored in the power supply controller.

10. The particle beam irradiation system according to claim 1, wherein the operating control data is constituted by a plurality of sets of module data including initial acceleration control data, a plurality of sets of extraction control data for extracting ion beams of a plurality of energy levels, a plurality of sets of energy change control data for interconnecting the plurality of sets of extraction control data, and a plurality of sets of deceleration control data corresponding to the respective extraction energy levels in the plurality of sets of extraction control data, and the controller is configured to conduct extraction control of the beams of the plurality of energy levels by combining the plurality of sets of module data, and enable rapid shift to deceleration control from whatever energy level by having the deceleration control data corresponding to the respective extraction energy levels in the plurality of sets of extraction control data.

11. The particle beam irradiation system according to claim 10, wherein the plurality of sets of deceleration control data are each constructed to have values corresponding to the respective extraction energy levels in the plurality of sets of extraction control data as initial data values, and to have values corresponding to incident energy level of the synchrotron as final data values.

12. The particle beam irradiation system according to claim 10, wherein the controller comprises:

a timing system configured to output a plurality of control timing signals to manage control timing of the devices constituting the synchrotron; and a power supply controller configured to control each of the devices constituting the synchrotron, wherein the initial acceleration control data, plurality of sets of extraction control data, plurality of sets of energy change control data, and plurality of sets of deceleration control data that constitute the operating control data are stored in the power supply controller, and wherein the power supply controller receives the plurality of control timing signals output from the timing system, and in accordance with the control timing signals, selects and updates the initial acceleration control data, the plurality of sets of extraction control data, the plurality of sets of energy change control data and the plurality of sets of deceleration control data.

13. The particle beam irradiation system according to claim 12, wherein the controller further comprises:

an interlock system configured to output an extraction control command for permitting a start of extraction parameter setting control in the synchrotron, an energy change command that is output in accordance with elapsed-time information on ion beam irradiated to the patient, a deceleration control command that is output in accordance with a state of devices including the synchrotron and the irradiation apparatus and constituting the particle beam irradiation system, and an irradiation completion command indicating that the irradiation has been completed, and wherein in accordance with the extraction control command, energy change command, deceleration control command, and irradiation completion command that are output from the interlock system, the timing system selects an appropriate control timing signal from the plurality of control timing signals and outputs the selected timing signal.

14. The particle beam irradiation system according to claim 12, wherein the controller further comprises:

an interlock system configured to output the deceleration control command in a case that the amount of beam charge stored within the synchrotron is insufficient for the irradiation with the beam of next energy level after completion of extraction control of the beam of a certain energy level, as well as in a case that the next target energy level is absent after completion of extraction control of the beam of a certain energy level, wherein upon receiving the deceleration control command, the timing system selects a deceleration control startup timing signal from the plurality of control timing signals and outputs the deceleration control startup timing signal, and wherein upon receiving the deceleration control startup timing signal, the power supply controller selects from the plurality of sets of deceleration control data the deceleration control data corresponding to the energy level upon completion of extraction control, and shifts to deceleration control.

15. The particle beam irradiation system according to claim 14, wherein
the interlock system is configured to output the deceleration control command in case of trouble with devices that constitute the particle beam irradiation system including the synchrotron and the irradiation apparatus, and
wherein upon receiving the deceleration control startup timing signal from the timing system, the power supply controller updates currently operative control data, then selects from the plurality of sets of deceleration control data the deceleration control data corresponding to the reached energy level after the control of the update, and shifts to deceleration control.

16. The particle beam irradiation system according to claim 14, wherein
the interlock system is configured to output the energy change command in the case that the next target energy level is present after completion of extraction control of the beam of a certain energy level, or that the reached energy level after completion of initial acceleration control or completion of energy change control disagrees with the next target energy level,
wherein upon receiving the energy change command, the timing system selects the appropriate energy change control timing signal from the plurality of control timing signals and outputs the energy change control timing signal, and
wherein upon receiving the energy change control timing signal, the power supply controller selects from the plurality of sets of energy change control data the energy change control data corresponding to the certain energy level or reached energy level, and shifts to energy change control.

17. The particle beam irradiation system according to claim 10, wherein
the initial acceleration control data, the plurality of sets of extraction control data, the plurality of sets of energy change control data and the plurality of sets of deceleration control data that constitute the operating control data are constituted by time-series data relating to a current/voltage which is a control quantity assigned directly to the devices constituting the synchrotron.

18. The particle beam irradiation system according to claim 10, wherein the controller comprises:
a storage device in which control data that includes the initial acceleration control data, the plurality of sets of extraction control data, the plurality of sets of energy change control data and the plurality of sets of deceleration control data that constitute the operating control data, and that enables extraction of beams of all energy levels corresponding to irradiation parameters for a plurality of patients assumed is stored as module data; and
a power supply controller configured to control each of the devices constituting the synchrotron,
wherein when irradiation parameters for a specific patient are assigned for irradiation setup, the controller selects appropriate control data from the module data stored in the storage device, stores the selected control data into the power supply controller to construct the operating control data.

19. A particle beam irradiation system, comprising:
a synchrotron constructed to accelerate and extract an ion beam;
an irradiation apparatus adapted to irradiate the ion beam extracted from the synchrotron;
a storage device in which control data that enables extraction of beams of all energy levels corresponding to irradiation parameters for a plurality of patients is stored as module data, the control data including a plurality of sets of initial acceleration control data, a plurality of sets of extraction control data, a plurality of sets of energy change control data, and a plurality of sets of deceleration control data that correspond to ion beams of a plurality of energy levels;
a power supply controller configured to control devices constituting the synchrotron; and
a particle beam irradiation system controller configured to select appropriate control data from the module data stored in the storage device when irradiation parameters for a specific patient are assigned for irradiation setup, store the selected control data into the power supply controller, and construct operating control data for the constituent devices of the synchrotron,
wherein the operating control data comprises a plurality of sets of deceleration control data to enable rapid shifting to deceleration control from an energy level of the plurality of energy levels.

20. A method for operating a particle beam irradiation system comprising a synchrotron constructed to accelerate and extract an ion beam, and an irradiation apparatus adapted to irradiate the ion beam extracted from the synchrotron, the operating method comprising;
constructing operating control data for devices constituting the synchrotron in such a manner as to control extraction of beams of a plurality of energy levels in one operating cycle of the synchrotron and to enable rapid shifting to deceleration control from an energy level of the plurality of energy levels; and
controlling the constituent devices of the synchrotron by using the operating control data,
wherein the operating control data comprises a plurality of sets of deceleration control data to enable the rapid shifting to deceleration control from an energy level of the plurality of energy levels.

21. The particle beam irradiation system operating method according to claim 20, further comprising:
constructing the operating control data according to multi-energy extraction control pattern data corresponding to the beam extraction control of the plurality of energy levels,
the multi-energy extraction control pattern data including a plurality of acceleration control sections for accelerating the beam to predetermined extraction energy levels and a plurality of extraction control sections for extracting the beam that has been accelerated to the predetermined energy levels,
the plurality of sets of deceleration control data corresponding to the respective extraction energy levels in the plurality of extraction control sections;
conducting extraction control of the beam of the plurality of energy levels by using the multi-energy extraction control pattern data to control the constituent devices; and
enabling a rapid shift to deceleration control from whatever energy level of the plurality of energy levels by using the plurality of sets of deceleration control data corresponding to the respective extraction energy levels in the plurality of extraction control sections to control the constituent devices.

22. The particle beam irradiation system operating method according to claim 20, wherein
when shift from the control of extraction at a certain energy level to deceleration control is conducted, after completion updating of currently ongoing control data, deceleration control data corresponding to an immediately previous extraction energy level is selected and the shift to deceleration control is conducted.

23. The particle beam irradiation system operating method according to claim 21, wherein
the operating control data and the plurality of sets of deceleration control data are constituted by time-series data relating to a current/voltage, which is a control quantity assigned directly to the devices constituting the synchrotron.

24. The particle beam irradiation system operating method according to claim 20, wherein
the operating control data is constituted by a plurality of sets of module control data including initial acceleration control data, a plurality of sets of extraction control data for extracting ion beams of a plurality of energy levels, a plurality of sets of energy change control data for interconnecting the plurality of sets of extraction control data, and a plurality of sets of deceleration control data corresponding to the respective extraction energy levels in the plurality of sets of extraction control data, and
extraction control of the beam of the plurality of energy levels is conducted by combining the plurality of sets of module data, and rapid shift to deceleration control from whatever energy level is enabled by having the deceleration control data corresponding to the respective energy levels in the plurality of sets of extraction control data.

25. The particle beam irradiation system operating method according to claim 24, wherein
control data that includes the initial acceleration control data, the plurality of sets of extraction control data, the plurality of sets of energy change control data and the plurality of sets of deceleration control data that constitute the operating control data, and that enables extraction of beams of all energy levels corresponding to irradiation parameters for a plurality of patients assumed is previously prepared as module data; and
when irradiation parameters for a specific patient are assigned, appropriate control data is selected from the module data to construct the operating control data.

* * * * *